(12) United States Patent
Nishi et al.

(10) Patent No.: US 9,751,880 B2
(45) Date of Patent: Sep. 5, 2017

(54) ELECTROPHOTOGRAPHIC PHOTOSENSITIVE MEMBER, PROCESS CARTRIDGE, ELECTROPHOTOGRAPHIC APPARATUS, AND IMIDE COMPOUND

(71) Applicant: CANON KABUSHIKI KAISHA, Tokyo (JP)

(72) Inventors: Masashi Nishi, Susono (JP); Kunihiko Sekido, Suntou-gun (JP); Michiyo Sekiya, Atami (JP); Kei Tagami, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/919,112

(22) Filed: Oct. 21, 2015

(65) Prior Publication Data
US 2016/0115163 A1    Apr. 28, 2016

(30) Foreign Application Priority Data
Oct. 24, 2014    (JP) .................. 2014-217359

(51) Int. Cl.
*G03G 5/14*    (2006.01)
*C07D 471/06*    (2006.01)

(52) U.S. Cl.
CPC .......... *C07D 471/06* (2013.01); *G03G 5/142* (2013.01)

(58) Field of Classification Search
CPC .................................................. G03G 5/142
See application file for complete search history.

(56) References Cited

U.S. PATENT DOCUMENTS

| | | | | |
|---|---|---|---|---|
| 5,645,965 A * | 7/1997 | Duff | ............................ | C09B 5/62 430/58.7 |
| 5,756,744 A * | 5/1998 | Duff | ...................... | C07D 519/00 546/34 |
| 6,593,046 B2 * | 7/2003 | Sorriero | .............. | C08G 73/1082 430/64 |
| 6,794,102 B2 * | 9/2004 | Bender | ................. | G03G 5/0661 430/56 |
| 7,011,916 B2 * | 3/2006 | Bender | ................. | G03G 5/0661 430/56 |
| 7,371,492 B2 * | 5/2008 | Ferrar | ..................... | G03G 5/102 430/123.4 |
| 7,449,268 B2 * | 11/2008 | Bender | ................. | C07D 209/48 430/58.3 |
| 7,541,124 B2 * | 6/2009 | Molaire | ................... | G03G 5/056 430/123.4 |
| 7,964,328 B2 * | 6/2011 | Ferrar | ................... | G03G 5/0571 430/123.4 |
| 2004/0013959 A1 * | 1/2004 | Bender | ................. | G03G 5/0661 430/56 |
| 2014/0004456 A1 * | 1/2014 | Okuda | .................... | G03G 15/00 430/56 |

FOREIGN PATENT DOCUMENTS

| | | | |
|---|---|---|---|
| CA | 2514508 C | * | 5/2008 |
| JP | 2005154409 A | * | 6/2005 |
| JP | 2012137667 A | * | 7/2012 |
| JP | 2014-029480 A | | 2/2014 |

OTHER PUBLICATIONS

English language machine translation of JP 2005-154409 (Jun. 2005).*

* cited by examiner

*Primary Examiner* — Christoper Rodee
(74) *Attorney, Agent, or Firm* — Canon U.S.A., Inc. IP Division

(57) ABSTRACT

An electrophotographic photosensitive member includes, in the following order, a support member, an undercoat layer adjacent to the support member, and a photosensitive layer adjacent to the undercoat layer. The undercoat layer contains a polymer produced by polymerizing a composition containing a crosslinking agent and a compound expressed by general formula (1):

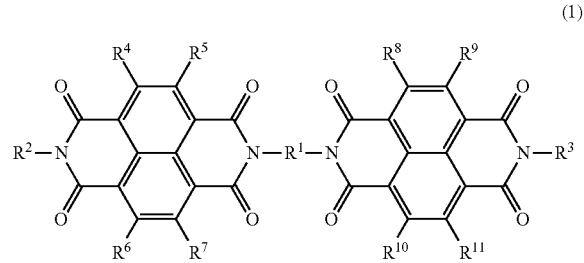

(1)

wherein $R^1$ to $R^{11}$ are defined in the specification.

5 Claims, 5 Drawing Sheets

ELECTROPHOTOGRAPHIC PHOTOSENSITIVE MEMBER, PROCESS CARTRIDGE, ELECTROPHOTOGRAPHIC APPARATUS, AND IMIDE COMPOUND

BACKGROUND OF THE INVENTION

Field of the Invention

The present application relates to an electrophotographic photosensitive member, a process cartridge, an electrophotographic apparatus, and an imide compound.

Description of the Related Art

Electrophotographic photosensitive members used in process cartridges and electrophotographic apparatuses typically include on a support member a photosensitive layer containing a charge generating material that is an organic photoconductive material.

The sensitivity of the charge generating material used in the photosensitive layer is being increased. Unfortunately, charge generation is increased with increasing sensitivity, and accordingly, charges become likely to be retained in the photosensitive layer. This is a cause of positive ghost. Positive ghost is a phenomenon that occurs in output images, in which only the portion irradiated with light at the time of the previous rotation of the electrophotographic photosensitive member has a higher density.

In order to suppress such positive ghost, Japanese Patent Laid-Open No. 2014-29480 discloses a technique in which an undercoat layer containing an electron transport material is formed between the support member and the photosensitive layer. This patent document discloses that positive ghost can be suppressed more effectively by adding a polymer of a composition containing the electron transport material, a crosslinking agent and a resin to prevent the structure derived from the electron transport material from being unevenly distributed in the undercoat layer.

According to a study by the present inventors, the electrophotographic photosensitive member of this disclosure is improved in terms of suppression of positive ghost and can provide satisfactory image quality. With growing recent demands for a longer-life electrophotographic photosensitive member and improved image quality, however, suppression of positive ghost at higher level is desirable.

SUMMARY OF THE INVENTION

The present application provides an electrophotographic photosensitive member improved in terms of suppression of positive ghost in repeated use thereof, and a process cartridge and an electrophotographic apparatus each including the electrophotographic photosensitive member. The present application further provides an imide compound that can suppress positive ghost.

According to an aspect of the present application, there is provided an electrophotographic photosensitive member including, in the following order, a support member, an undercoat layer adjacent to the support member and a photosensitive layer adjacent to the undercoat layer. The undercoat layer contains a polymer produced by polymerizing a composition containing a crosslinking agent and a compound expressed by the following general formula (1):

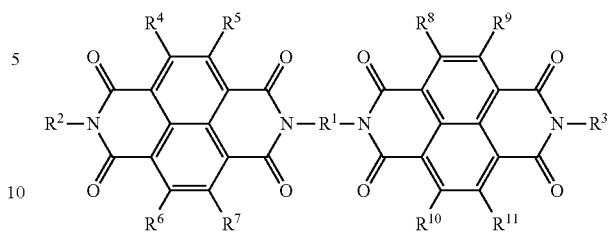

In general formula (1), $R^1$ represents one selected from the group consisting of alkylene group, cycloalkylene group, arylene group, heterocycle group, and alkylene-derived groups having a main chain in which one of the carbon atoms is replaced with a species selected from among O, S, and $NR^{12}$. $R^{12}$ is selected from hydrogen atom, alkyl group, and aryl group. The alkylene group, the cycloalkylene group, the arylene group and the heterocycle group may have a substituent selected from the group consisting of alkyl group having a carbon number in the range of 1 to 6, benzyl group, acyl group, alkoxy group, alkoxycarbonyl group, phenyl group, cyano group, nitro group, and halogen atoms. $R^2$ and $R^3$ each represent one selected from the group consisting of alkyl group, aryl group, and alkyl-derived groups having a main chain in which one of the carbon atoms is replaced with a species selected from among O, S, and $NR^{13}$ where $R^{13}$ is selected from hydrogen and alkyl. $R^2$ and $R^3$ has a polymerizable functional group selected from the group consisting of hydroxy group, thiol group, amino group and carboxy group and may have a substituent selected from the group consisting of alkyl group having a carbon number in the range of 1 to 6, acyl, alkoxy group, alkoxycarbonyl group, phenyl group, cyano group, nitro group, and halogen toms. $R^4$ to $R^{11}$ each represent one selected from the group consisting of hydrogen atom, halogen atoms, cyano group, nitro group, alkyl group, and aryl group. The alkyl group and aryl group each may have a substituent selected from the group consisting of alkyl group, acyl group, alkoxy group, alkoxycarbonyl group, cyano group, nitro group, and halogen atoms.

According to another aspect of the application, there is provided a process cartridge capable of being removably attached to an electrophotographic apparatus. The process cartridge includes the above-described electrophotographic photosensitive member and at least one device selected from the group consisting of a charging device, a developing device, a transfer device, and a cleaning device. The electrophotographic photosensitive member and the device are held in one body.

Also, an electrophotographic apparatus is provided. The electrophotographic apparatus includes the above-described electrophotographic photosensitive member, a charging device, an exposure device, a developing device, and a transfer device.

Furthermore, an imide compound expressed by the above described general formula (1) is provided.

Further features of the present invention will become apparent from the following description of exemplary embodiments with reference to the attached drawings.

DESCRIPTION OF THE EMBODIMENTS

Figure 1:
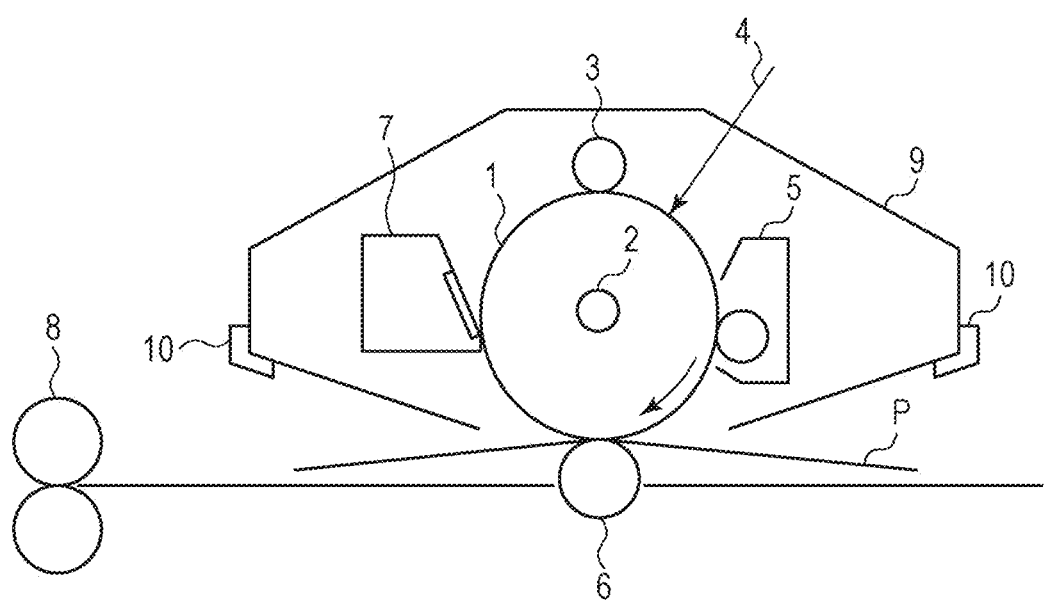
FIG. 1 is a schematic view of the structure of an electrophotographic apparatus provided with a process cartridge including an electrophotographic photosensitive member.

The electrophotographic photosensitive member according to an embodiment of the present application include an undercoat layer containing a polymer produced by polymerizing a composition containing a crosslinking agent and a compound (electron transport material) expressed by the following general formula (1):

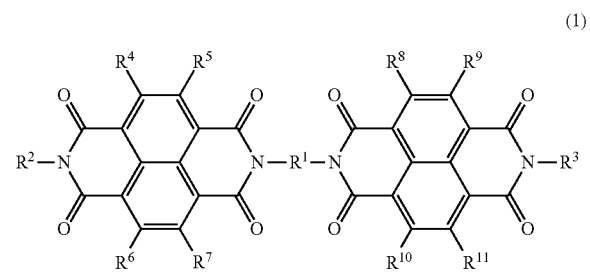

In general formula (1), $R^1$ represents one selected from the group consisting of alkylene group, cycloalkylene group, arylene group, heterocycle group, and alkylene-derived groups having a main chain in which one of the carbon atoms is replaced with a species selected from among O, S, and $NR^{12}$. $R^{12}$ is selected from among hydrogen atom, alkyl group, and aryl group. The alkylene group, the cycloalkylene group, the arylene group and the heterocycle group may have a substituent selected from the group consisting of alkyl group having a carbon number of 1 to 6, benzyl group, acyl group, alkoxy group, alkoxycarbonyl group, phenyl group, cyano group, nitro group, and halogen atoms.

$R^2$ and $R^3$ each represent one selected from the group consisting of alkyl group, aryl group, and alkyl-derived groups having a main chain in which one of the carbon atoms is replaced with a species selected from among O, S, and $NR^{13}$ where $R^{13}$ is selected from hydrogen atom and alkyl group. $R^2$ and $R^3$ has a polymerizable functional group selected from the group consisting of hydroxy group, thiol group, amino group and carboxy group and may have a substituent selected from the group consisting of alkyl group having a carbon number of 1 to 6, acyl group, alkoxy group, alkoxycarbonyl group, phenyl group, cyano group, nitro group, and halogen atoms.

$R^4$ to $R^{11}$ each represent one selected from the group consisting of hydrogen atom, halogen atoms, cyano group, nitro group, alkyl group, and aryl group. The alkyl group and the aryl group each may have a substituent selected from the group consisting of alkyl group, acyl group, alkoxy group, alkoxycarbonyl group, cyano group, nitro group, and halogen atoms.

The present inventors assume as below the reason why positive ghost is suppressed by adding the above-described polymer to the undercoat layer.

If the undercoat layer containing an electron transport material has a defect, the charge transport material is unevenly distributed, or the defect itself induces the formation of an electron trap. This is probably a cause of positive ghost. If an electron trap is formed in the undercoat layer, electron transportability becomes likely to decrease, and the undercoat layer is likely to have a residual charge. The residual charge can be accumulated by repeated use over a long time, thereby causing positive ghost. It is assumed that such a defect in the undercoat layer is formed more easily as the variation in volume of the materials of the undercoat layer by polymerization becomes larger.

The electron transport material expressed by general formula (1) has a molecular structure in which two skeletons capable of transporting electrons are joined with $R^1$ including a spacer. This structure enables the variation in volume by polymerization to be reduced in comparison with the structures in which the molecule has a single skeleton capable of transporting electrons. The structure of general formula (1) is effective in reducing the defect in the undercoat layer and in suppressing positive ghost particularly when the undercoat layer has a large thickness.

The content in the undercoat layer of the polymer of the composition containing the compound expressed by general formula (1) may be in the range of 50% to 100% by mass relative to the total mass of the undercoat layer. Advantageously, it is in the range of 80% to 100% by mass.

Electron Transport Material

In the present embodiment, the undercoat layer contains a polymer (cured product) of a composition containing a crosslinking agent and a compound expressed by general formula (1). The compound of general formula (1) has already been described above.

Advantageously, $R^1$ of the compound of general formula (1) is selected from among the groups expressed by general formulas (2), (3) and (4). These groups prevent the formation of electron traps, thereby further suppressing positive ghost.

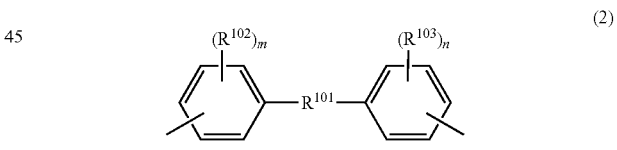

In general formula (2), $R^{101}$ represents one selected from the group consisting of O, S, $SO_2$, $NR^{104}$, carbonyl group, alkylene group, and arylene group. The alkylene group and the arylene group each may have a substituent selected from the group consisting of alkyl group having a carbon number of 1 to 5, phenyl group, and halogen atoms. $R^{102}$ and $R^{103}$ each represent one selected from the group consisting of alkyl group having a carbon number of 1 to 3, alkoxy group, alkoxycarbonyl group, cyano group, nitro group, and halogen atoms. m representing the number of $R^{102}$ and n representing the number of $R^{103}$ may be the same as or different from each other.

$R^{104}$ is selected from hydrogen atom, alkyl group, and aryl group. m and n are each an integer of 0 to 4. When m and n are 0, $(R^{102})m$ and $(R^{103})n$ each represent hydrogen atom.

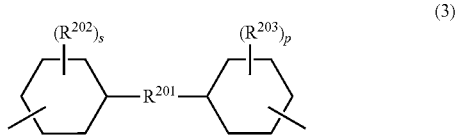

(3)

In general formula (3), $R^{201}$ represents one selected from the group consisting of O, S, $SO_2$, $NR^{204}$, carbonyl group, alkylene group, and arylene group. The alkylene group and the arylene group each may have a substituent selected from the group consisting of alkyl group having a carbon number of 1 to 5, phenyl group, and halogen atoms. $R^{202}$ and $R^{203}$ each represent one selected from the group consisting of alkyl group having a carbon number of 1 or 2, alkoxy group, alkoxycarbonyl group, and halogen atoms. s representing the number of $R^{202}$ and p representing the number of $R^{203}$ may be the same as or different from each other. $R^{204}$ is selected from hydrogen atom, alkyl group, and aryl group. s and p are each an integer of 0 to 4. When s and p are 0, $(R^{202})$s and $(R^{203})$p each represent hydrogen atom.

(4)

In general formula (4), $R^{301}$ represents hydrogen atom, $R^{302}$ represents alkylene group or arylene group, and $R^{303}$ represents alkyl group. Each of the alkylene group, arylene group and alkyl group may have a substituent selected from the group consisting of O, S, alkyl group having a carbon number of 1 or 2, alkoxycarbonyl group, and phenyl group.

Advantageously, $R^2$ and $R^3$ of the compound of general formula (1) are each expressed by the following general formula (5).

(5)

In general formula (5), $R^{401}$ represents hydrogen atom, and $R^{402}$ and $R^{403}$ each represent alkyl group having hydroxy group or aryl group having hydroxy group. Each of the alkyl group and aryl group may have at least one substituent selected from the group consisting of alkyl group having a carbon number of 1 to 6, alkoxy group, alkoxycarbonyl group, phenyl group, and halogen atoms.

In the present embodiment, it is desirable that the polymer of the composition containing the crosslinking agent and the compound of general formula (1) be not in a state of particles in the undercoat layer. More specifically, "being not in a state of particles" means that when the section of the undercoat layer is observed by SEM, shapes derived from particles are not found. In order to allow the polymer to be in such a state, the undercoat layer may be formed by applying a liquid in which the polymer is dissolved.

Crosslinking Agent

The crosslinking agent is polymerized with (cures) the compound of general formula (1) or crosslinks the compound of general formula (1). More specifically, compounds described in, for example, "Crosslinking Agent Handbook" (in Japanese, edited by Shinzo Yamashita and Tosuke Kaneko, published by Taiseisha in 1981) may be used as the crosslinking agent.

Examples of the crosslinking agent include, but are not limited to, the following isocyanate compounds and amine compounds. A plurality of crosslinking agents may be used in combination.

Advantageously, the isocyanate compound has two or more isocyanate groups or blocked isocyanate groups. Isocyanate compounds having 3 to 6 isocyanate groups or blocked isocyanate groups are more advantageous. Examples of such an isocyanate compounds include benzene triisocyanate, methylbenzene triisocyanate, triphenylmethane triisocyanate, lysine triisocyanate, isocyanurate-modified, biuret-modified, allophanate-modified compounds of diisocyanates, such as tolylene diisocyanate, hexamethylene diisocyanate, dicyclohexylmethane diisocyanate, naphthalene diisocyanate, diphenylmethane diisocyanate, isophorone diisocyanate, xylylene diisocyanate, 2,2,4-trimethylhexamethylene diisocyanate, methyl-2,6-diisocyanate hexanoate, and norbornane diisocyanate, and trimethylolpropane adducts or pentaerythritol adducts of these diisocyanates. Isocyanurate-modified compounds and adducts are particularly advantageous.

Exemplary commercially available isocyanate compounds that can be used as the crosslinking agent include isocyanate-based crosslinking agents, such as DURANATE series MFK-60B and SBA-70B produced by Asahi Kasei and DESMODUR series BL 3175 and BL 3475 produced by Sumika Bayer Urethane; amino-based crosslinking agents, such as U-VAN series 20SE60 and 220 produced by Mitsui Chemicals and Super Beckamine series L-125-60 and G-821-60 produced by DIC; and acrylic crosslinking agents, such as FANCRYL series FA-129AS and FA-731A produced by Hitachi Chemical.

Advantageously, the amine compound used as the crosslinking agent has two or more N-methylol groups or alkyletherified N-methylol groups. Examples of such an amine compound include methylolated melamines, methylolated guanamines, methylolated urea derivatives, methylolated ethylene urea derivatives, methylolated glycolurils, compounds having an alkyletherified methylol site, and derivatives of these compounds.

Exemplary commercially available amine compounds that can be used as the crosslinking agent include Super Melami No. 90 (produced by NOF); Super Beckamine (R) series TD-139-60, L-105-60, L-127-60, L-110-60, J-820-60, G-821-60, L-148-55, 13-535, L-145-60, and TD-126 (each produced by DIC); U-VAN 2020 (produced by Mitsui Chemicals); Sumitex Resin M-3 (produced by Sumitomo Chemical); and NIKALAC series MW-30, MW-390, MX-750LM, BL-60, BX-4000, MX-270, and MX-290 (produced by Nippon Carbide).

Resin

In an embodiment, the composition may contain a resin having a polymerizable functional group. The resin having a polymerizable functional group refers to a resin whose polymerizable functional group can be polymerized with (cure) the compound of general formula (1). Examples of the polymerizable functional group include hydroxy, thiol, amino, carboxy, and methoxy.

Examples of the resin having a polymerizable functional group include, but are not limited to, polyether-polyol resin, polyester-polyol resin, polyacrylic polyol resin, polyvinyl alcohol resin, polyvinyl acetal resin, polyamide resin, carboxy-containing resin, polyamine resin, and polythiol resin. Some of these resins may be used in combination.

Exemplary commercially available resins having a polymerizable functional group include polyether-polyol resin, such as AQD-457 and AQD-473 (produced by Nippon Polyurethane Industry) and SANNIX GP series GP-400 and GP-700 (produced by Sanyo Chemical Industries); polyester-polyol resin, such as Phthalkyd W 2343 (produced by Hitachi Chemical), WATERSOL series S-118 and CD-520 (produced by DIC), and HARIDIP WH-1188 (produced by Harima Chemicals); polyacrylic polyol resin, such as BURNOCK series WE-300 and WE-304 (produced by DIC); polyvinyl alcohol resin, such as POVAL PVA-203 (produced by Kuraray); polyvinyl acetal resin, such as BX-1, BM-1, KS-1, and KS-5 (produced by Sekisui Chemical); polyamide resin, such as Toresin FS-350 (produced by Nagase Chemtex); carboxy-containing resin, such as AQUALIC (produced by Nippon Shokubai) and FINELEX SG 2000 (produced by Namariichi); polyamine resin, such as LUCKAMIDE (produced by DIC); and polythiol resin, such as QE-340M (produced by Toray). Among these, polyvinyl acetal resin and polyester-polyol resin are advantageous from the viewpoint of polymerization.

The resin having a polymerizable functional group may have a weight average molecular weight of 5,000 to 400,000, such as 5,000 to 300,000.

From the viewpoint of suppressing positive ghost, the total mass of the crosslinking agent and the resin having a polymerizable functional group is desirably in the range of 0.5 to 2.5 relative to the mass of the compound expressed by general formula (1).

In addition to the above-described polymer, the undercoat layer may further contain other resin (not having a polymerizable functional group), organic particles, inorganic particles, a levelling agent or any other additive for facilitating the formation of the undercoat layer and improving the electrical properties of the undercoat layer. The content of these additional materials in the undercoat layer is desirably 50% by mass or less, such as 20% by mass or less, relative to the total mass of the undercoat layer.

The undercoat layer may be formed by applying an undercoat liquid containing the compound of general formula (1) and the crosslinking agent and drying the coating film of the liquid. When the coating film of the undercoat liquid is dried, the compound of general formula (1) and the crosslinking agent are polymerized (sequentially polymerized). By applying an energy such as heat or light at this time, polymerization reaction (curing reaction) is accelerated.

Although a large thickness of the undercoat layer is effective in preventing charges from entering from the support member, a thick undercoat layer tends to retain charges therein. This is a cause of ghost. The undercoat layer containing the above-described polymer is effective in suppressing ghost even if it has a large thickness. Desirably, the thickness of the undercoat layer is in the range of 0.1 μm to 10.0 μm, such as in the range of 0.5 μm to 5.0 μm.

The solvent used in the undercoat liquid applied for forming the undercoat layer may be an alcohol-based solvent, a sulfoxide-based solvent, a ketone-based solvent, an ether-based solvent, an ester-based solvent, or an aromatic hydrocarbon.

Examples of the electron transport material (compound expressed by general formula (1)) are shown in, but are not limited to, Tables 1 to 11. Some of these electron transport materials may be used in combination.

TABLE 1

| Exemplified compound | R4 | R5 | R6 | R7 | R8 | R9 | R10 | R11 | R1 | R2 | R3 |
|---|---|---|---|---|---|---|---|---|---|---|---|
| 101 | H | H | H | H | H | H | H | H | 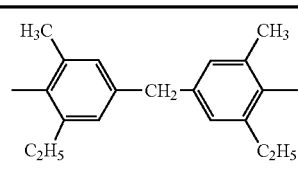 | 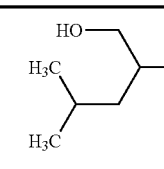 | 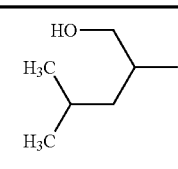 |
| 102 | H | H | H | H | H | H | H | H | 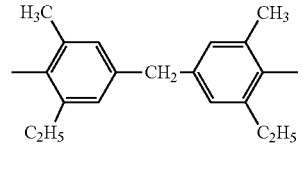 | 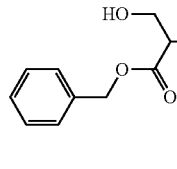 | 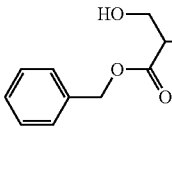 |
| 103 | H | H | H | H | H | H | H | H | 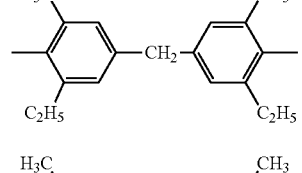 | 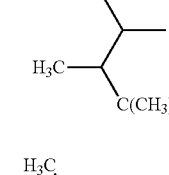 | 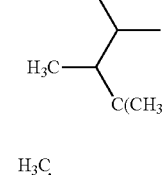 |
| 104 | H | H | H | H | H | H | H | H | 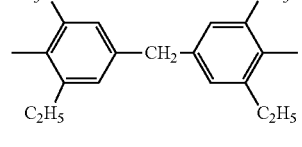 | 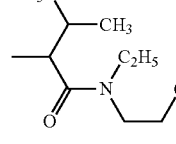 | 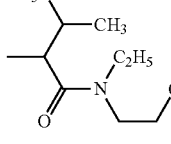 |

TABLE 1-continued
| Exemplified compound | R4 | R5 | R6 | R7 | R8 | R9 | R10 | R11 | R1 | R2 | R3 |
|---|---|---|---|---|---|---|---|---|---|---|---|
| 105 | H | H | H | H | H | H | H | H | 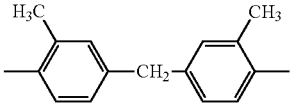 | 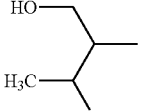 | 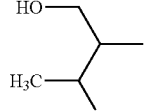 |
| 106 | H | H | H | H | H | H | H | H | 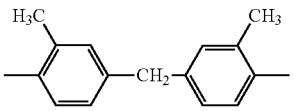 | 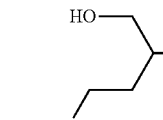 | 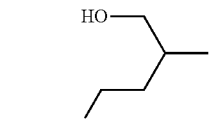 |
| 107 | H | H | H | H | H | H | H | H | 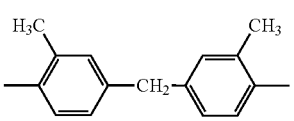 | 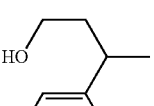 | 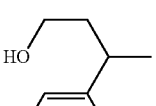 |
| 108 | H | H | H | H | H | H | H | H |  | 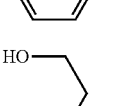 | 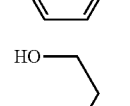 |
| 109 | H | H | H | H | H | H | H | H |  | 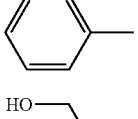 | 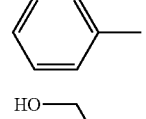 |
| 110 | H | H | H | H | H | H | H | H | 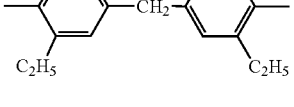 | 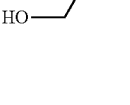 | 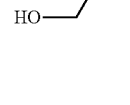 |
TABLE 2
| Exemplified compound | R4 | R5 | R6 | R7 | R8 | R9 | R10 | R11 | R1 | R2 | R3 |
|---|---|---|---|---|---|---|---|---|---|---|---|
| 111 | H | H | H | H | H | H | H | H | 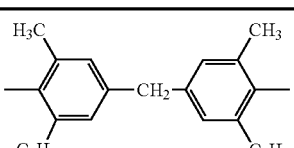 | 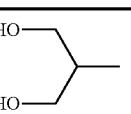 | 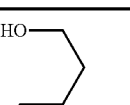 |
| 112 | Br | H | H | Br | Br | H | H | Br | 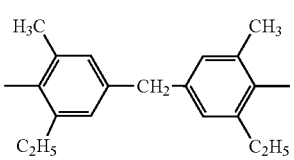 | 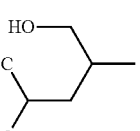 | 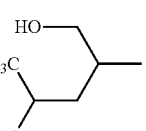 |

TABLE 2-continued
| Exemplified compound | R4 | R5 | R6 | R7 | R8 | R9 | R10 | R11 | R1 | R2 | R3 |
|---|---|---|---|---|---|---|---|---|---|---|---|
| 113 | NO₂ | H | H | NO₂ | NO₂ | H | H | NO₂ | 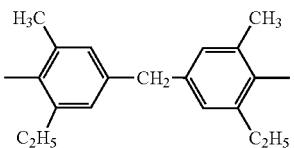 | 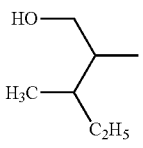 | 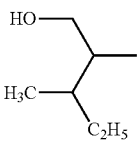 |
| 114 | CH₃ | H | H | CH₃ | CH₃ | H | H | CH₃ | 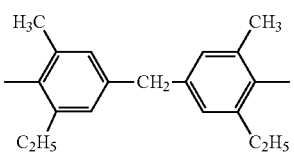 | 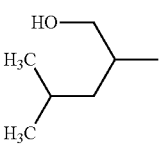 | 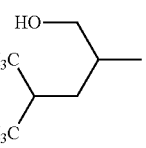 |
| 115 | CN | H | H | CN | CN | H | H | CN | 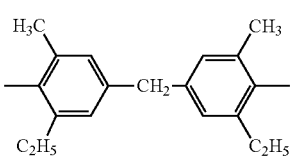 | 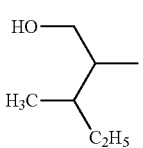 | 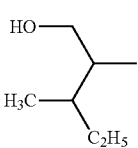 |
| 116 | H | H | H | H | H | H | H | H | 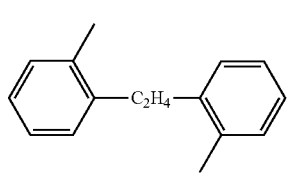 | 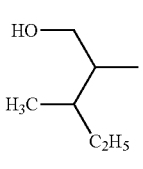 | 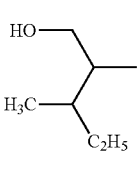 |
| 117 | H | H | H | H | H | H | H | H | 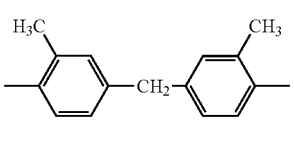 | 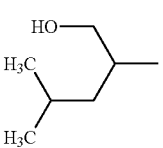 | 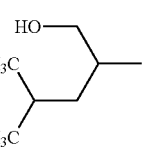 |
| 118 | H | H | H | H | H | H | H | H | 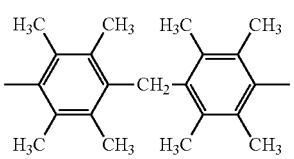 | 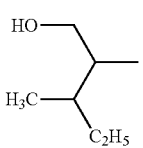 | 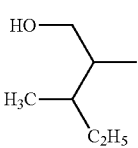 |
| 119 | H | H | H | H | H | H | H | H | 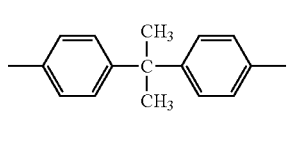 | 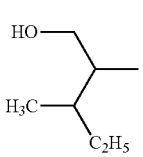 | 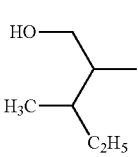 |
| 120 | H | H | H | H | H | H | H | H | 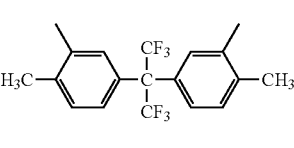 | 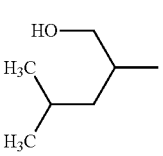 | 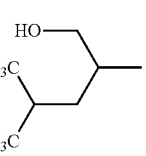 |
| 121 | H | H | H | H | H | H | H | H | 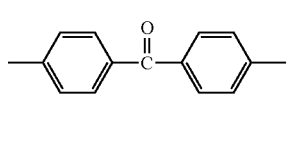 | 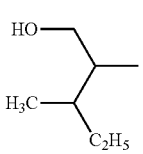 | 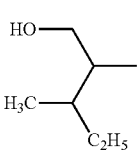 |

TABLE 2-continued
| Exemplified compound | R4 | R5 | R6 | R7 | R8 | R9 | R10 | R11 | R1 | R2 | R3 |
|---|---|---|---|---|---|---|---|---|---|---|---|
| 122 | H | H | H | H | H | H | H | H | 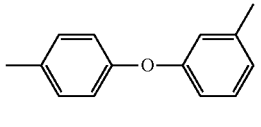 | 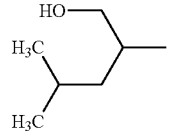 | 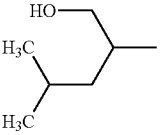 |
| 123 | H | H | H | H | H | H | H | H | 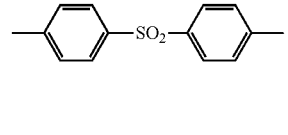 | 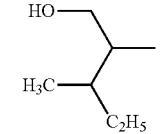 | 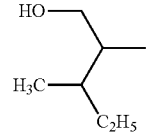 |
TABLE 3
| Exemplified compound | R4 | R5 | R6 | R7 | R8 | R9 | R10 | R11 | R1 |
|---|---|---|---|---|---|---|---|---|---|
| 124 | H | H | H | H | H | H | H | H | 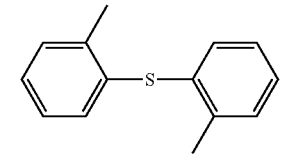 |
| 125 | H | H | H | H | H | H | H | H | 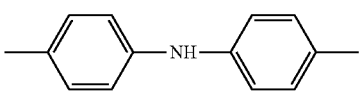 |
| 126 | H | H | H | H | H | H | H | H | 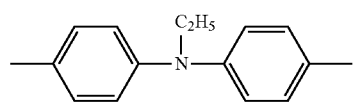 |
| 127 | H | H | H | H | H | H | H | H | 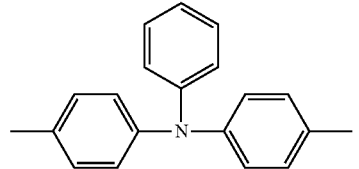 |
| 128 | H | H | H | H | H | H | H | H | 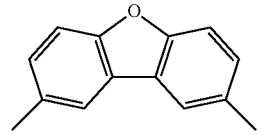 |
| 129 | H | H | H | H | H | H | H | H | 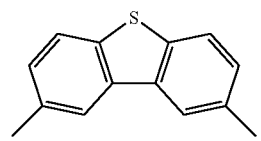 |
| 130 | H | H | H | H | H | H | H | H | 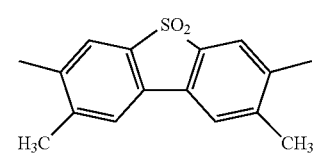 |

TABLE 3-continued
| | | | | | | | | | |
|---|---|---|---|---|---|---|---|---|---|
| 131 | H | H | H | H | H | H | H | H | 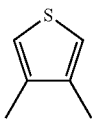 |
| 132 | H | H | H | H | H | H | H | H | 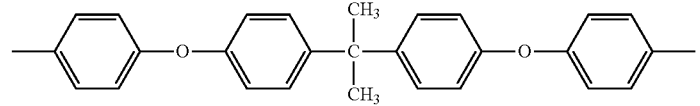 |
| 133 | H | H | H | H | H | H | H | H | 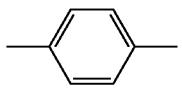 |
| 134 | H | H | H | H | H | H | H | H | 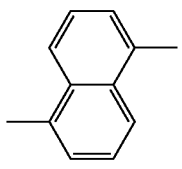 |
| 135 | H | H | H | H | H | H | H | H | 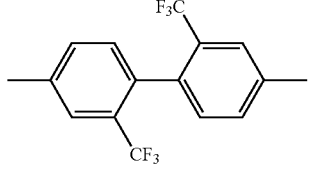 |
| 136 | H | H | H | H | H | H | H | H | 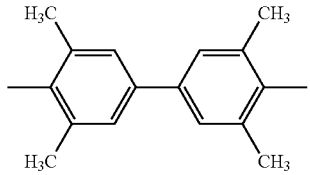 |
| Exemplified compound | R2 | R3 |
|---|---|---|
| 124 | 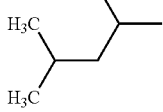 | 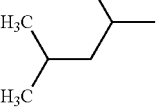 |
| 125 | 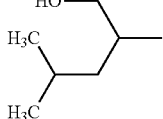 | 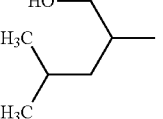 |
| 126 | 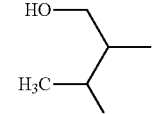 | 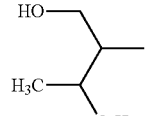 |
| 127 | 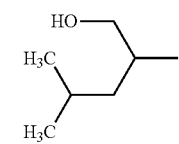 | 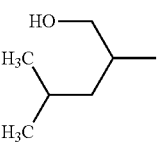 |

TABLE 3-continued

| | | | |
|---|---|---|---|
| 128 | (4-methyl-2-(hydroxymethyl)pentyl structure) | (4-methyl-2-(hydroxymethyl)pentyl structure) | |
| 129 | (4-methyl-2-(hydroxymethyl)pentyl structure) | (4-methyl-2-(hydroxymethyl)pentyl structure) | |
| 130 | (4-methyl-2-(hydroxymethyl)pentyl structure) | (4-methyl-2-(hydroxymethyl)pentyl structure) | |
| 131 | (4-methyl-2-(hydroxymethyl)pentyl structure) | (4-methyl-2-(hydroxymethyl)pentyl structure) | |
| 132 | (2-methyl-3-ethyl-hydroxymethyl structure with $C_2H_5$) | (2-methyl-3-ethyl-hydroxymethyl structure with $C_2H_5$) | |
| 133 | (4-methyl-2-(hydroxymethyl)pentyl structure) | (4-methyl-2-(hydroxymethyl)pentyl structure) | |
| 134 | (4-methyl-2-(hydroxymethyl)pentyl structure) | (4-methyl-2-(hydroxymethyl)pentyl structure) | |
| 135 | (4-methyl-2-(hydroxymethyl)pentyl structure) | (4-methyl-2-(hydroxymethyl)pentyl structure) | |
| 136 | (4-methyl-2-(hydroxymethyl)pentyl structure) | (4-methyl-2-(hydroxymethyl)pentyl structure) | |

TABLE 4
| Exemplified compound | R4 | R5 | R6 | R7 | R8 | R9 | R10 | R11 | R1 | R2 | R3 |
|---|---|---|---|---|---|---|---|---|---|---|---|
| 137 | H | H | H | H | H | H | H | H | 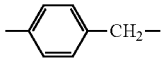 | 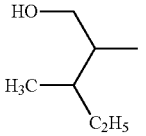 | 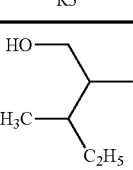 |
| 138 | H | H | H | H | H | H | H | H |  | 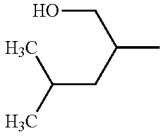 | 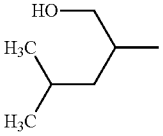 |
| 139 | H | H | H | H | H | H | H | H | 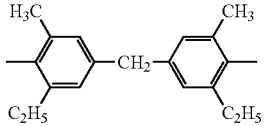 | 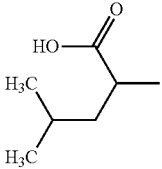 | 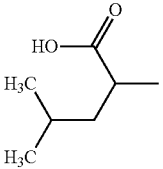 |
| 140 | H | H | H | H | H | H | H | H |  | 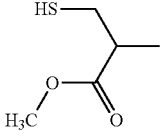 | 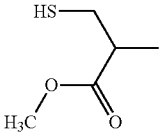 |
| 141 | H | H | H | H | H | H | H | H |  | 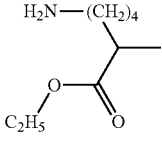 | 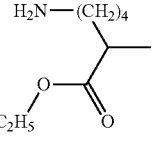 |
| 142 | H | H | H | H | H | H | H | H | 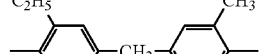 | 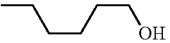 | 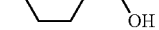 |
| 143 | H | H | H | H | H | H | H | H |  | 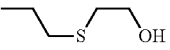 | 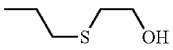 |
| 144 | H | H | H | H | H | H | H | H |  | 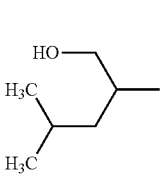 | 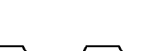 |
| 145 | H | H | H | H | H | H | H | H | 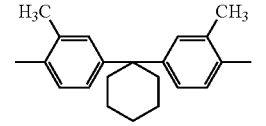 | 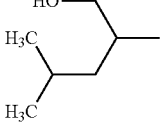 | 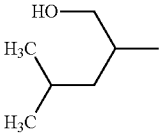 |
| 146 | H | H | H | H | H | H | H | H | 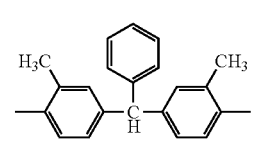 | 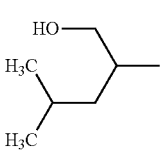 | 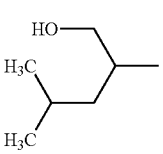 |

TABLE 4-continued
| Exemplified compound | R4 | R5 | R6 | R7 | R8 | R9 | R10 | R11 | R1 | R2 | R3 |
|---|---|---|---|---|---|---|---|---|---|---|---|
| 147 | H | H | H | H | H | H | H | H | 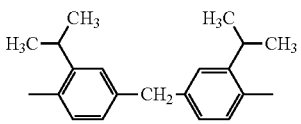 | 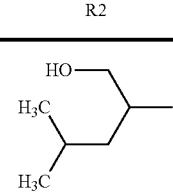 | 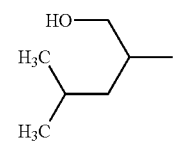 |
| 148 | H | H | H | H | H | H | H | H | 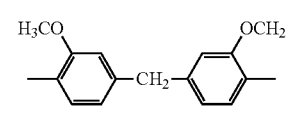 | 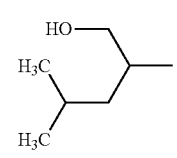 | 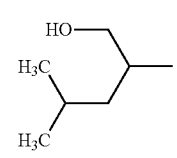 |
| 149 | H | H | H | H | H | H | H | H | 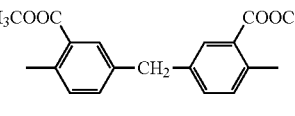 | 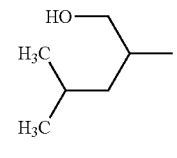 | 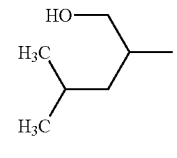 |
TABLE 5
| Exemplified compound | R4 | R5 | R6 | R7 | R8 | R9 | R10 | R11 | R1 | R2 | R3 |
|---|---|---|---|---|---|---|---|---|---|---|---|
| 150 | H | H | H | H | H | H | H | H | 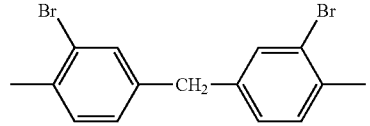 | 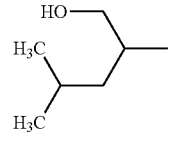 | 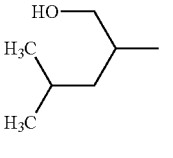 |
| 151 | H | H | H | H | H | H | H | H | 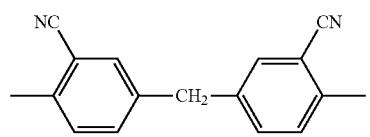 | 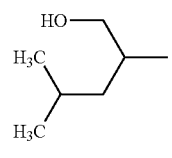 | 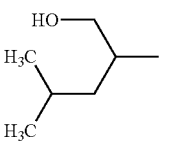 |
| 152 | H | H | H | H | H | H | H | H | 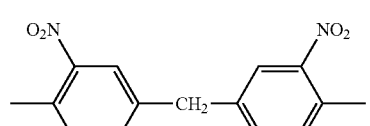 | 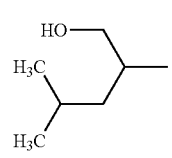 | 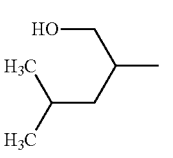 |
| 153 | H | H | H | H | H | H | H | H | 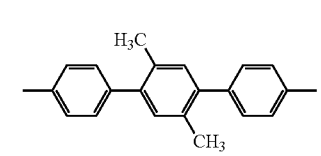 | 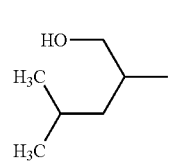 | 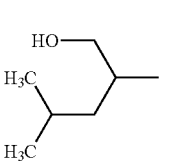 |

TABLE 6
| Exemplified compound | R4 | R5 | R6 | R7 | R8 | R9 | R10 | R11 | R1 | R2 | R3 |
|---|---|---|---|---|---|---|---|---|---|---|---|
| 201 | H | H | H | H | H | H | H | H | 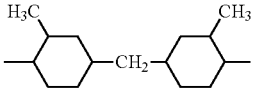 | 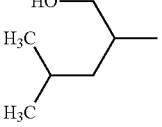 | 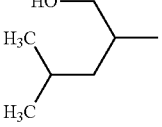 |
| 202 | H | H | H | H | H | H | H | H | 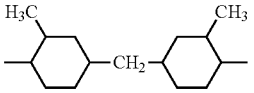 | 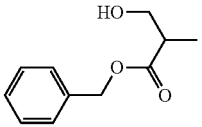 | 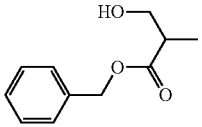 |
| 203 | H | H | H | H | H | H | H | H | 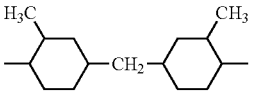 | 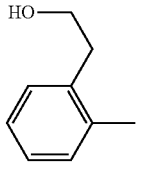 | 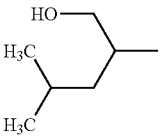 |
| 204 | H | H | H | H | H | H | H | H | 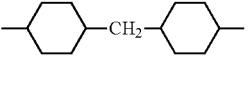 | 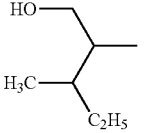 | 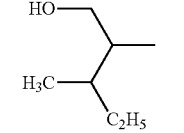 |
| 205 | H | H | H | H | H | H | H | H | 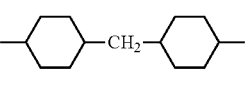 | 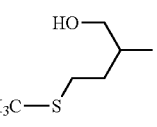 | 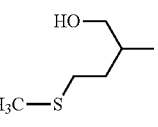 |
| 206 | H | H | H | H | H | H | H | H | 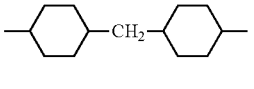 | 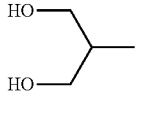 | 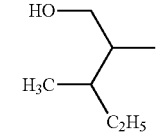 |
| 207 | Br | H | H | Br | Br | H | H | Br | 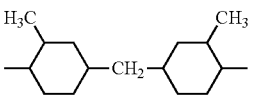 | 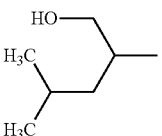 | 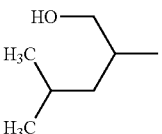 |
| 208 | NO$_2$ | H | H | NO$_2$ | NO$_2$ | H | H | NO$_2$ | 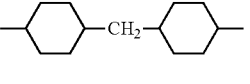 | 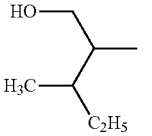 | 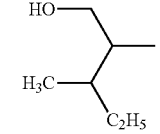 |
| 209 | CH$_3$ | H | H | CH$_3$ | CH$_3$ | H | H | CH$_3$ | 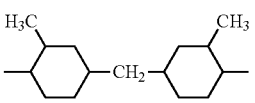 | 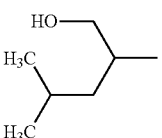 | 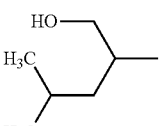 |
| 210 | CN | H | H | CN | CN | H | H | CN | 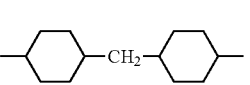 | 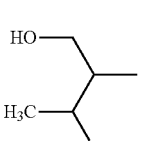 | 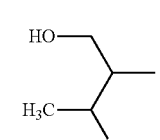 |

TABLE 6-continued
| Exemplified compound | R4 | R5 | R6 | R7 | R8 | R9 | R10 | R11 | R1 | R2 | R3 |
|---|---|---|---|---|---|---|---|---|---|---|---|
| 211 | H | H | H | H | H | H | H | H | 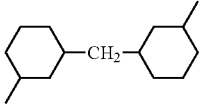 | 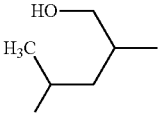 | 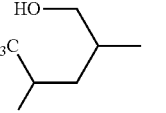 |
| 212 | H | H | H | H | H | H | H | H | 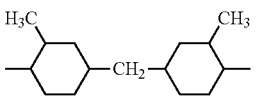 | 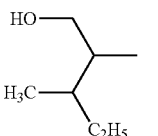 | 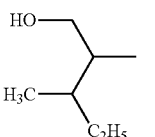 |
| 213 | H | H | H | H | H | H | H | H | 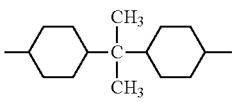 | 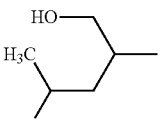 | 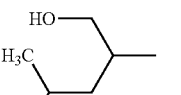 |
TABLE 7
| Exemplified compound | R4 | R5 | R6 | R7 | R8 | R9 | R10 | R11 | R1 | R2 | R3 |
|---|---|---|---|---|---|---|---|---|---|---|---|
| 214 | H | H | H | H | H | H | H | H | 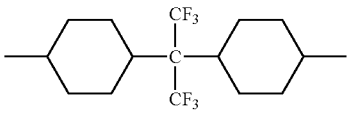 | 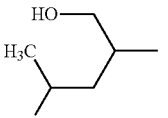 | 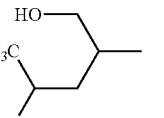 |
| 215 | H | H | H | H | H | H | H | H | 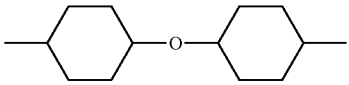 | 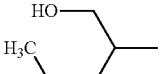 | 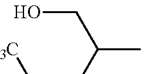 |
| 216 | H | H | H | H | H | H | H | H | 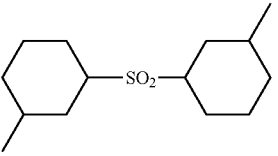 | 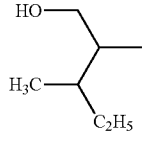 | 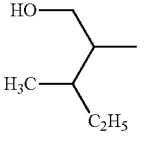 |
| 217 | H | H | H | H | H | H | H | H | 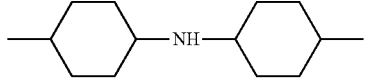 | 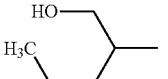 | 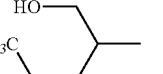 |
| 218 | H | H | H | H | H | H | H | H | 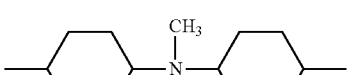 | 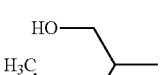 | 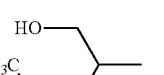 |

TABLE 7-continued
| Exemplified compound | R4 | R5 | R6 | R7 | R8 | R9 | R10 | R11 | R1 | R2 | R3 |
|---|---|---|---|---|---|---|---|---|---|---|---|
| 219 | H | H | H | H | H | H | H | H | 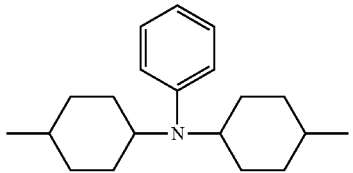 | 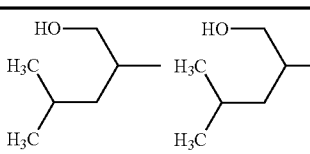 | 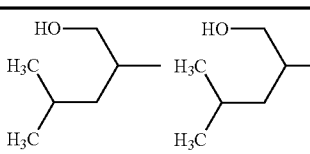 |
| 220 | H | H | H | H | H | H | H | H | 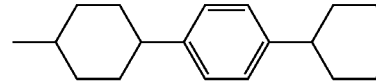 | 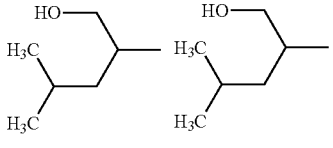 | 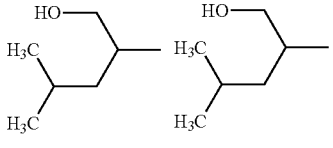 |
| 221 | H | H | H | H | H | H | H | H | 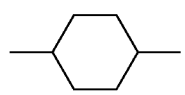 | 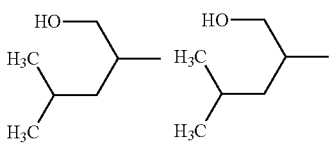 | 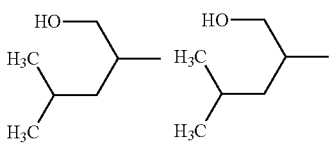 |
| 222 | H | H | H | H | H | H | H | H | 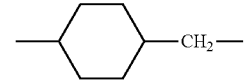 | 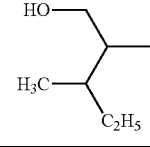 | 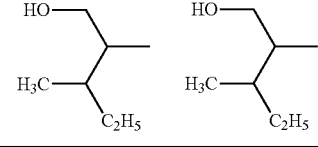 |
TABLE 8
| Exemplified compound | R4 | R5 | R6 | R7 | R8 | R9 | R10 | R11 | R1 | R2 | R3 |
|---|---|---|---|---|---|---|---|---|---|---|---|
| 223 | H | H | H | H | H | H | H | H | 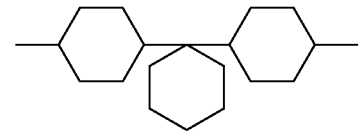 | 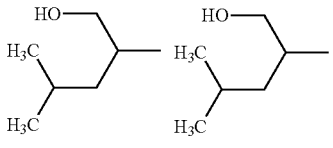 | 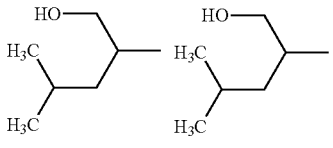 |
| 224 | H | H | H | H | H | H | H | H | 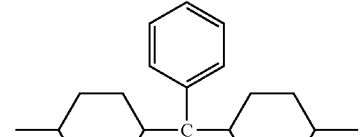 | 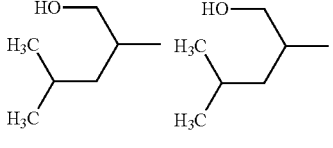 | 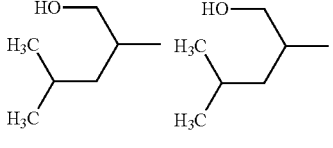 |
| 225 | H | H | H | H | H | H | H | H | 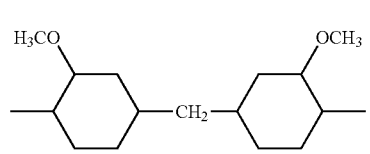 | 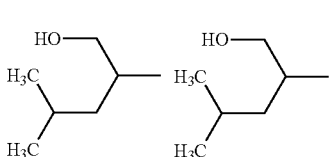 | 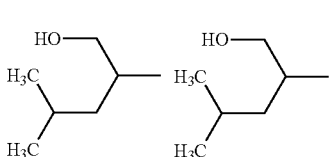 |
| 226 | H | H | H | H | H | H | H | H | 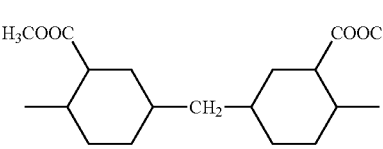 | 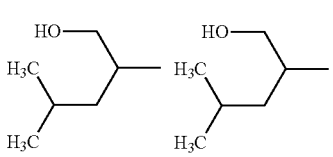 | 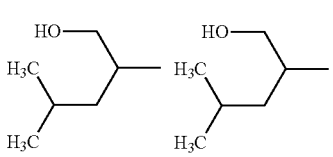 |

TABLE 8-continued
| Exemplified compound | R4 | R5 | R6 | R7 | R8 | R9 | R10 | R11 | R1 | R2 | R3 |
|---|---|---|---|---|---|---|---|---|---|---|---|
| 227 | H | H | H | H | H | H | H | H | 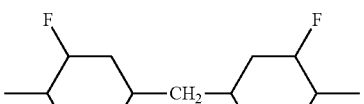 | 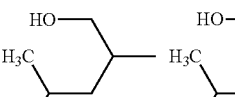 | 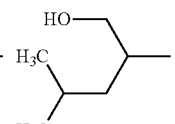 |
| 228 | H | H | H | H | H | H | H | H | 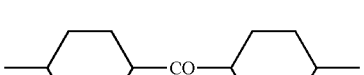 |  | 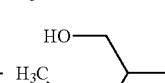 |
| 229 | H | H | H | H | H | H | H | H |  |  | 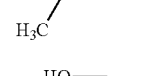 |
TABLE 9
| Exemplified compound | R4 | R5 | R6 | R7 | R8 | R9 | R10 | R11 | R1 | R2 | R3 |
|---|---|---|---|---|---|---|---|---|---|---|---|
| 301 | H | H | H | H | H | H | H | H | 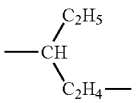 | 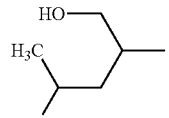 | 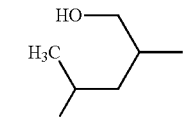 |
| 302 | H | H | H | H | H | H | H | H | 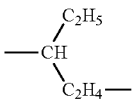 | 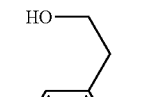 | 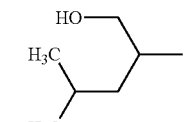 |
| 303 | H | H | H | H | H | H | H | H | 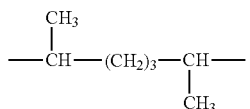 | 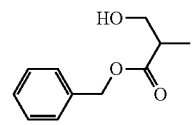 | 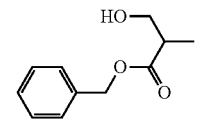 |
| 304 | H | H | H | H | H | H | H | H | 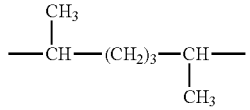 | 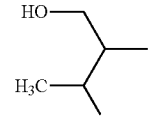 | 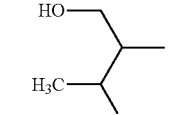 |
| 305 | H | H | H | H | H | H | H | H | 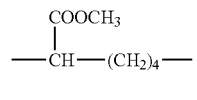 | 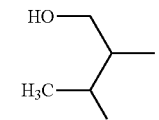 | 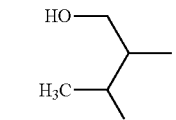 |

TABLE 9-continued

| Exemplified compound | R4 | R5 | R6 | R7 | R8 | R9 | R10 | R11 | R1 | R2 | R3 |
|---|---|---|---|---|---|---|---|---|---|---|---|
| 306 | H | H | H | H | H | H | H | H | —CH(COOCH₃)—(CH₂)₄— | HOCH₂CH(OH)CH₃ type (2-methyl-1,3-propanediol residue) | 2-methyl-2-ethyl... (HO—CH₂—C(CH₃)(C₂H₅)—) |
| 307 | H | H | H | H | H | H | H | H | —CH(COOCH₃)—(CH₂)₃—CH(COOCH₃)— | HO—CH₂—CH(CH₃)—CH₂—S—CH₃ | HO—CH₂—CH(CH₃)—CH₂—S—CH₃ |
| 308 | H | H | H | H | H | H | H | H | —CH(COOCH₃)—(CH₂)₃—CH(COOCH₃)— | HO—CH₂—CH₂—(2-methylphenyl) | HO—CH₂—CH₂—(2-methylphenyl) |
| 309 | H | H | H | H | H | H | H | H | —C(=O)—CH₂—S—CH₂—C(=O)— | HO—CH₂—CH(CH₃)—CH₂—CH(CH₃)₂ | HO—CH₂—CH(CH₃)—CH₂—CH(CH₃)₂ |
| 310 | H | H | H | H | H | H | H | H | —CH(COOCH₃)—(CH₂—S)₂—CH₂—CH(COOCH₃)— | HO—CH₂—CH(CH₃)—CH₂—CH(CH₃)₂ | HO—CH₂—CH(CH₃)—CH₂—CH(CH₃)₂ |
| 311 | Br | H | H | Br | Br | H | H | Br | —CH(C₂H₅)(C₂H₄—) | HO—CH₂—CH(CH₃)—CH₂—CH(CH₃)₂ | HO—CH₂—CH(CH₃)—CH₂—CH(CH₃)₂ |

TABLE 10

| Exemplified compound | R4 | R5 | R6 | R7 | R8 | R9 | R10 | R11 | R1 | R2 | R3 |
|---|---|---|---|---|---|---|---|---|---|---|---|
| 312 | NO₂ | H | H | NO₂ | NO₂ | H | H | NO₂ | —CH(CH₃)—(CH₂)₃—CH(CH₃)— | HO—CH₂—CH(CH₃)—CH(C₂H₅)—CH₃ | HO—CH₂—CH(CH₃)—CH(C₂H₅)—CH₃ |
| 313 | CH₃ | H | H | CH₃ | CH₃ | H | H | CH₃ | —CH(COOCH₃)—(CH₂)₂—CH(COOCH₃)— | HO—CH₂—CH(CH₃)—CH₂—CH(CH₃)₂ | HO—CH₂—CH(CH₃)—CH₂—CH(CH₃)₂ |

TABLE 10-continued
| Exemplified compound | R4 | R5 | R6 | R7 | R8 | R9 | R10 | R11 | R1 | R2 | R3 |
|---|---|---|---|---|---|---|---|---|---|---|---|
| 314 | CN | H | H | CN | CN | H | H | CN | 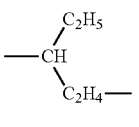 | 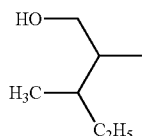 | 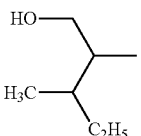 |
| 315 | H | H | H | H | H | H | H | H | 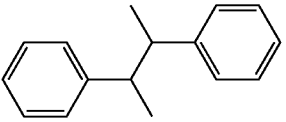 | 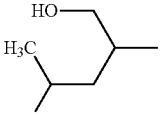 | 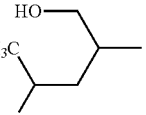 |
| 316 | H | H | H | H | H | H | H | H | 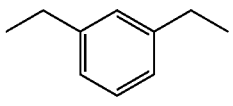 | 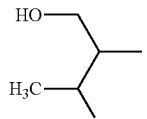 | 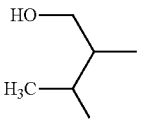 |
| 317 | H | H | H | H | H | H | H | H | 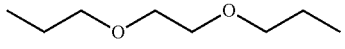 | 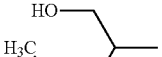 | 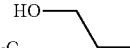 |
| 318 | H | H | H | H | H | H | H | H | 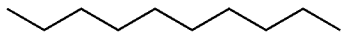 | 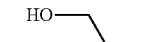 | 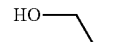 |
TABLE 11
| Exemplified compound | R4 | R5 | R6 | R7 | R8 | R9 | R10 | R11 | R1 | R2 | R3 |
|---|---|---|---|---|---|---|---|---|---|---|---|
| 319 | H | H | H | H | H | H | H | H | 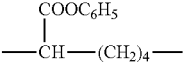 | 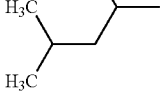 | 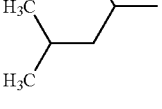 |
| 320 | H | H | H | H | H | H | H | H | 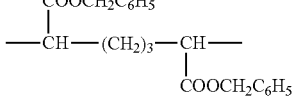 | 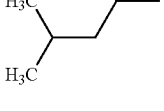 | 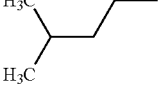 |
| 321 | H | H | H | H | H | H | H | H | 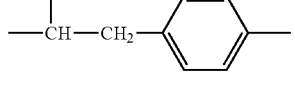 | 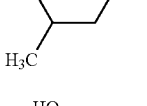 | 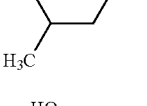 |
| 322 | H | H | H | H | H | H | H | H | 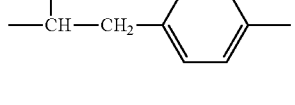 | 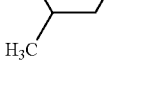 | 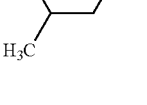 |

TABLE 11-continued

| Exemplified compound | R4 | R5 | R6 | R7 | R8 | R9 | R10 | R11 | R1 | R2 | R3 |
|---|---|---|---|---|---|---|---|---|---|---|---|
| 323 | H | H | H | H | H | H | H | H | 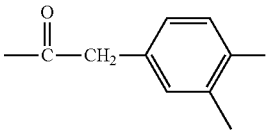 | 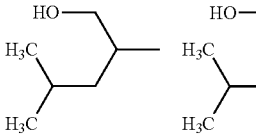 | 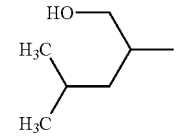 |
| 324 | H | H | H | H | H | H | H | H | 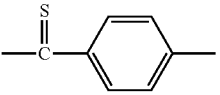 | 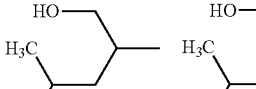 | 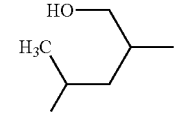 |

A precursor of the compound expressed by general formula (1) (precursor of the electron transport material) may be synthesized by, but not limited to, known processes disclosed in, for example, Japanese Patent Laid-Open No. 2001-265031, J. Am. Chem. Soc., 120, 3231 (1998), or Tetrahedron Letters, 42, 3559 (2001). The precursor may be synthesized using naphthalenetetracarboxylic acid dianhydride available from Tokyo Chemical Industry, Sigma-Aldrich Japan, or Johnson Matthey Japan.

The compound of general formula (1) has a polymerizable functional group (hydroxy, thiol, amino, or carboxy). The polymerizable functional group can be introduced to the precursor of the compound of general formula (1) by either of the following two methods. The polymerizable functional group may be directly introduced to the precursor of the compound of general formula (1); or a structure having the polymerizable functional group or a functional group capable of being a precursor of the polymerizable functional group is introduced to the precursor of the compound of general formula (1). For the latter, an aryl group having a functional group may be introduced to a halogenated precursor of the compound of general formula (1) by cross coupling reaction with a palladium catalyst and a base. Alternatively, an alkyl group having a functional group may be introduced to a halogenated precursor of the compound of general formula (1) by cross coupling reaction with $FeCl_3$ catalyst and a base. An epoxy compound or $CO_2$ may be allowed to act on a halogenated precursor of the compound of general formula (1) after lithiation, thereby introducing hydroxyalkyl or carboxy. For synthesizing the precursor of the compound of general formula (1), there may be used a naphthalenetetracarboxylic acid dianhydride or monoamine derivative having the polymerizable functional group or a functional group capable of being a precursor of the polymerizable functional group.

The compounds used in the present embodiment can be identified by nuclear magnetic resonance spectroscopy (NMR) using an analyzer JMN-EX400 manufacture by JEOL and deuterated DMSO as a deuterated solvent.

The electrophotographic photosensitive member according to an embodiment includes a support member, an undercoat layer on the support member, and a photosensitive layer on the undercoat layer. The photosensitive layer may have a multilayer structure (function-separated structure) including a charge generating layer containing a charge generating material, and a charge transport layer containing a charge transport material. From the viewpoint of the properties of electrophotography, the photosensitive layer having a multilayer structure is desirably of a forward type including the charge generating layer and the charge transport layer in that order from the direction of the support member.

Figure 4A:
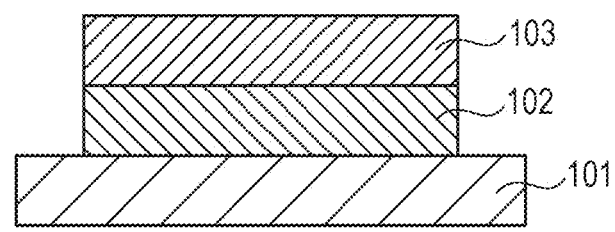
FIGS. 4A and 4B are representations of exemplary multilayer structures of the electrophotographic photosensitive member.
Figure 4B:
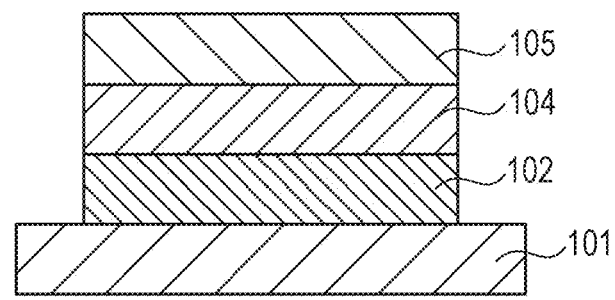

FIGS. 4A and 4B show exemplary multilayer structures of the electrophotographic photosensitive member. FIG. 4A shows a single-layer photosensitive layer 103 that is formed on an undercoat layer 102 on a support member 101. FIG. 4B shows a multilayer photosensitive layer including an undercoat layer 102 on a support member 101, a charge generating layer 104 on the undercoat layer 102, and a charge transport layer 105 on the charge generating layer 104.

The electrophotographic photosensitive member is typically in a cylindrical form in which a photosensitive layer (or a charge generating layer and a charge transport layer) is disposed over the periphery of the cylindrical support member, but may be in a belt form or a sheet form.

Support Member

The support member is desirably electrically conductive (electroconductive support member). For example, the support member may be made of a metal, such as aluminum, nickel, copper, gold, or iron, or an alloy thereof. Alternatively, an insulating support member made of, for example, polyester resin, a polycarbonate resin, a polyimide resin or glass may be coated with a metal thin film made of, for example, aluminum, silver or gold. The insulating support member may be coated with an electroconductive thin film made of, for example, indium oxide or tin oxide.

The support member may be subjected to surface treatment to improve the electrical properties and suppress the occurrence of interference fringes by electrochemical operation such as anodization, or wet honing, blast or cutting.

An electroconductive layer may be provided between the support member and the undercoat layer. The electroconductive layer can be formed by applying a coating liquid for forming the electroconductive layer containing electroconductive particles dispersed in a resin to the surface of the support member, and drying the coating film on the support member.

Examples of the electroconductive particles include carbon black, acetylene black, powder of metal such as aluminum, nickel, iron, Nichrome, copper, zinc or silver, and powder of a metal oxide such as electroconductive tin oxide or ITO.

The resin used in the electroconductive layer may be a polyester resin, a polycarbonate resin, a polyvinyl butyral resin, an acrylic resin, a silicone resin, an epoxy resin, a melamine resin, a urethane resin, a phenol resin, or an alkyd resin.

The solvent used in the coating liquid for the electroconductive layer may be an ether-based solvent, an alcohol-based solvent, a ketone-based solvent, or an aromatic hydrocarbon. The thickness of the electroconductive layer may be in the range of 0.2 µm to 40 µm, such as 1 µm to 35 µm or 5 µm to 30 µm.

Photosensitive Layer

A photosensitive layer (that may include a charge generating layer and a charge transport layer) is disposed on the undercoat layer. The charge generating layer and the charge transport layer each may include a plurality of layers. The charge generating layer contains a charge generating material and a binding resin.

Examples of the charge generating material include azo pigments, perylene pigments, anthraquinone derivatives, anthanthrone derivatives, dibenzpyrenequinone derivatives, pyranthrone derivatives, quinone pigments, indigoid pigments, phthalocyanine pigments, and perinone pigments. Among these, azo pigments and phthalocyanine pigments are advantageous. Advantageous phthalocyanine pigments include oxytitanium phthalocyanine, chlorogallium phthalocyanine, and hydroxygallium phthalocyanine.

Examples of the binding resin used in the charge generating layer include polymers or copolymers of vinyl compounds, such as styrene, vinyl acetate, vinyl chloride, acrylic acid esters, methacrylic acid esters, vinylidene fluoride, and trifluoroethylene; and polyvinyl alcohol, polyvinyl acetal, polycarbonate, polyester, polysulfone, polyphenylene oxide, polyurethane, cellulose resin, phenol resin, melamine resin, silicone resin, and epoxy resin. Among these, polyester, polycarbonate and polyvinyl acetal are advantageous.

In the charge generating layer, the mass ratio of the charge generating material to the binding resin may be in the range of 10/1 to 1/10, such as 5/1 to 1/5. The solvent used in the coating liquid for the charge generating layer may be an alcohol-based solvent, a ketone-based solvent, an ether-based solvent, an ester-based solvent, or an aromatic hydrocarbon. The thickness of the charge generating layer may be in the range of 0.05 µm to 5 µm.

The charge transport layer contains a charge transport material and a binding resin. Examples of the charge transport material include hydrazone compounds, styryl compounds, benzidine compounds, buthadiene compounds, enamines, triarylamine compounds, and triphenylamine. Alternatively, the charge transport material may be a polymer having a group derived from these compounds in the main chain or a side chain.

Examples of the binding resin used in the charge transport layer include polyester, polycarbonate, polymethacrylate, polyarylate, polysulfone, and polystyrene. Among these, polycarbonate and polyarylate are advantageous. The binding resin may have a weight average molecular weight in the range of 10,000 to 300,000.

In the charge transport layer, the mass ratio of the charge transport material to the binding resin may be in the range of 10/5 to 5/10, such as 10/8 to 6/10. The thickness of the charge transport layer may be in the range of 5 µm to 40 µm. The solvent used in the coating liquid for forming the charge transport layer may be an alcohol-based solvent, a ketone-based solvent, an ether-based solvent, an ester-based solvent, or an aromatic hydrocarbon.

An additional layer not containing the polymer produced by polymerizing the above-described composition, which may be called second undercoat layer, may be provided between the support member and the above-described undercoat layer or between the undercoat layer and the photosensitive layer.

The photosensitive layer (charge transport layer) may be provided thereon with a protective layer containing electroconductive particles or a charge transport material and a binding resin. The protective layer may further contain an additive such as a lubricant. The binding resin in the protective layer may have electrical conductivity or hole transportability. In this instance, the protective layer need not contain materials other than the binding resin, such as electroconductive particles and a hole transport material. The binding resin in the protective layer may be thermoplastic, or may be a resin cured by heat, light, or radiation (e.g. electron beam).

Each layer of the electrophotographic photosensitive member, such as the undercoat layer, the charge generating layer, and the charge transport layer, may be formed by the following process. The materials of each layer are dissolved and/or dispersed in a solvent to prepare a coating liquid. The coating liquid is applied to form a coating film, and the coating film is dried and/or cured. The coating liquid may be applied by immersion (immersion coating), spray coating, curtain coating, or spin coating. From the viewpoint of efficiency and productivity, immersion coating is advantageous.

Process Cartridge and Electrophotographic Apparatus

FIG. 1 is a schematic view of the structure of an electrophotographic apparatus provided with a process cartridge including an electrophotographic photosensitive member.

This electrophotographic photosensitive member 1 is driven for rotation on an axis 2 in the direction indicated by an arrow at a predetermined peripheral speed. The surface (periphery) of the electrophotographic photosensitive member 1 driven for rotation is uniformly charged to a predetermined positive or negative potential with a charging device 3 (for example, a contact-type primary charging device or a non-contact-type primary charging device). Then, the surface or periphery is exposed to light (image exposure light) 4 from an exposure device (not shown), such as a slit exposure device or a laser beam scanning exposure device. Thus electrostatic latent images corresponding to desired images are formed one after another on the surface of the electrophotographic photosensitive member 1.

The electrostatic latent images formed on the surface of the electrophotographic photosensitive member 1 are then developed into toner images with the toner contained in the developer in the developing device 5. The toner images on the surface of the electrophotographic photosensitive member 1 are transferred to a transfer medium P, such as a paper sheet, one after another from a transfer device 6, such as a transfer roller. The transfer medium P is fed to an abutting portion between the electrophotographic photosensitive member 1 and the transfer device 6 from a transfer medium feeder (not shown) in synchronization with the rotation of the electrophotographic photosensitive member 1.

The transfer medium P to which the toner images have been transferred is separated from the surface of the electrophotographic photosensitive member 1 and introduced into a fixing device 8, in which the toner images are fixed, thus being ejected as an image-formed article (printed matter or copy).

The surface of the electrophotographic photosensitive member 1 from which the toner images have been transferred is cleaned with a cleaning device 7, such as a cleaning blade, to remove therefrom the developer (toner) remaining after transfer. Subsequently, the electrophotographic photosensitive member 1 is subjected to pre-exposure (not shown) with the exposure device (not shown) to remove static electricity before being reused to form images. If the charging device 3 is a type of contact charging, such as a charging roller as shown in FIG. 1, pre-exposure is not necessarily required.

Some of the electrophotographic photosensitive member 1, the charging device 3, the developing device 5 and the cleaning device 7 may be combined in a single container as an integrated process cartridge. The process cartridge may be removably mounted to the electrophotographic apparatus. In the structure shown in FIG. 1, the electrophotographic photosensitive member 1, the charging device 3, the developing device 5 and the cleaning device 7 are integrated into a cartridge, and the cartridge is guided by a guide 10 such as a rail, thus being removably mounted as a process cartridge 9 in the electrophotographic apparatus.

EXAMPLES

The present application will be further described with reference to Examples below. The term "part(s)" used hereinafter refers to "part(s) by mass". First, an imide compound (electron transport material) expressed by general formula (1) is synthesized. The synthesized compound was subjected to NMR analysis under the above-described conditions.

Synthesis Examples

Figure 5:
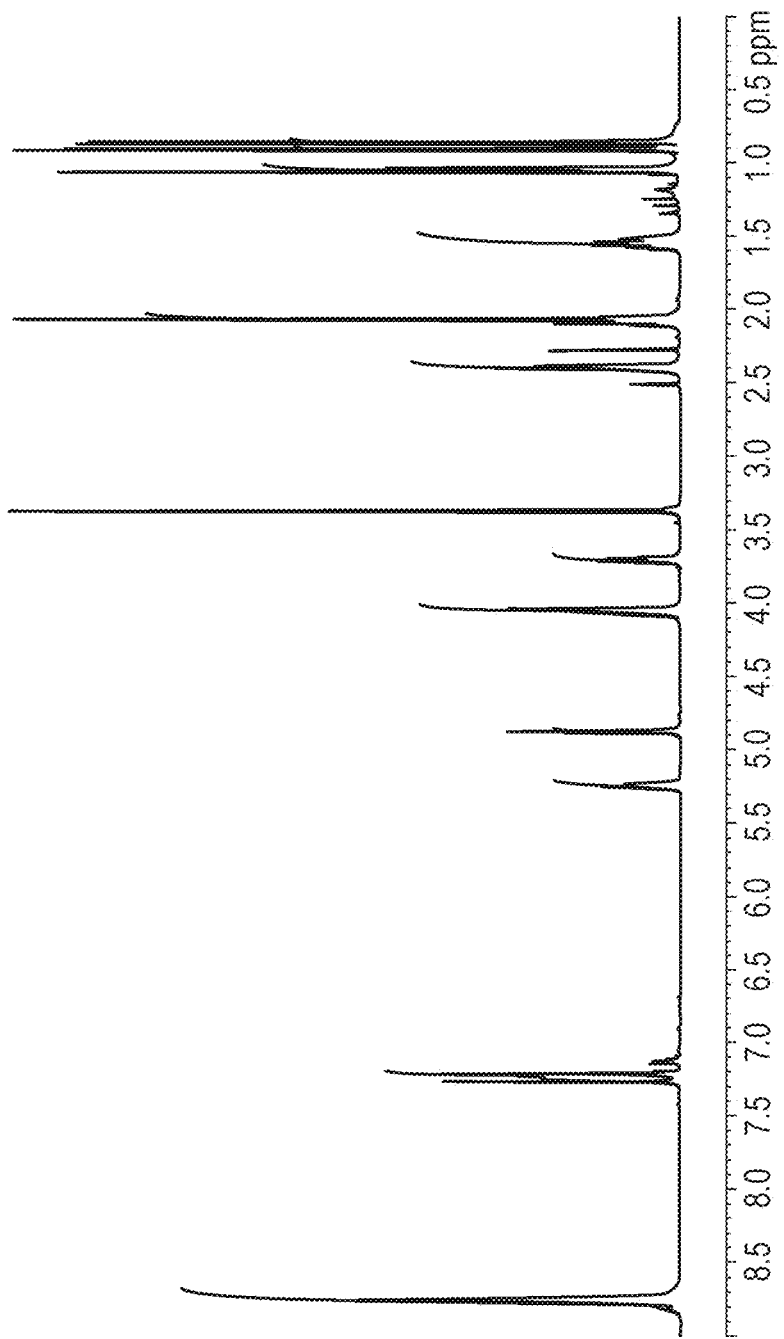
FIG. 5 is a $^1$H-NMR spectrum of a compound synthesized in an example.

In a nitrogen atmosphere, 5.4 parts of naphthalenetetracarboxylic acid dianhydride and 2.6 parts of L-lucinol were added to 200 parts of dimethylacetamide, followed by refluxing for 3 hours. Then, 2.9 parts of 4,4'-methylenebis (2-ethyl-6-methylaniline) was added, followed by refluxing for 3 hours. The reaction mixture was subjected to separation by silica gel column chromatography (eluent: ethyl acetate/toluene), and then the fraction containing a target compound was concentrated. The concentrated sample was subjected to recrystallization in an ethyl acetate/toluene mixed solution to yield 2.0 parts of the target compound. The resulting compound was subjected to NMR analysis and confirmed to be Exemplified Compound 101. The NMR spectrum thereof is shown in FIG. 5.

Then, electrophotographic photosensitive members were produced and evaluated.

Example 1

An aluminum cylinder (JIS-A3003 aluminum alloy) having a length of 260.5 mm and a diameter of 30 mm was used as a support member (electroconductive support member).

Then, 214 parts of oxygen-deficient tin oxide ($SnO_2$)-coated titanium oxide ($TiO_2$) particles as metal oxide particles, 132 parts of a phenol resin (product name: Plyophen J-325, produced by DIC, resin solid content: 60% by mass) and 98 parts of 1-methoxy-2-propanol were added into a sand mill containing 450 parts of glass beads of 0.8 mm in diameter, and were dispersed in each other to prepare a dispersion liquid for 4.5 hours at a rotation speed of 2000 rpm with cooling water set to 18° C. Then, the glass beads were removed from the dispersion liquid through a mesh (openings: 150 μm).

Silicone resin particles were added to the dispersion liquid, from which the glass beads had been removed, in a proportion of 10% by mass relative to the total mass of the metal oxide particles and the binding resin in the dispersion liquid. Also, a silicone oil was added to the dispersion liquid in a proportion of 0.01% by mass relative to the total mass of the metal oxide particles and the binding resin in the dispersion liquid, and the mixture was stirred to yield a coating liquid for forming an electroconductive layer. This coating liquid was applied to the surface of the support member by immersion. The resulting coating film was dried and cured by heating at 150° C. for 30 minutes to yield a 30 μm thick electroconductive layer. The silicone resin particles were a commercially available product TOSPEARL 120 (average particle size: 2 μm) produced by Momentive Performance Materials. The silicone oil was SH28PA produced by Dow Corning Toray.

Then, 4 parts of Exemplified Compound 101, 1.5 parts of a polyvinyl butyral resin (product name: BX-1, produced by Sekisui Chemical) being a polyvinyl acetal resin, and 0.0005 part of a catalyst zinc (II) octylate were dissolved in a mixed solution containing 100 parts of dimethylacetamide and 100 parts of tetrahydrofuran. To the resulting solution, blocked isocyanate (product name: BL 3175, produced by Sumika Bayer Urethane) was added in an amount of 6 parts in terms of solid to prepare a coating liquid for forming the undercoat layer. This coating liquid was applied to the surface of the electroconductive layer by immersion. The resulting coating film was cured by being heating at 160° C. for 40 minutes, thus forming a 2.0 μm thick undercoat layer.

Subsequently, there was prepared crystalline hydroxygallium phthalocyanine (charge generating material) whose CuKα X-ray diffraction spectrum has peaks at Bragg angles 2θ (±0.2°) of 7.5°, 9.9°, 12.5°, 16.3°, 18.6°, 25.1° and 28.3°. Into a sand mill containing glass beads of 1 mm in diameter were added 10 parts of the crystalline hydroxytitanium phthalocyanine, 5 parts of a polyvinyl butyral resin (product name: S-LEC BX-1, produced by Sekisui Chemical) and 250 parts of cyclohexanone. The materials were dispersed in each other in the sand mill for 2 hours. Then, 250 parts of ethyl acetate was added to the dispersion liquid to yield a coating liquid for forming a charge generating layer. This coating liquid was applied to the surface of the undercoat layer by immersion. The resulting coating film was dried at 95° C. for 10 minutes to yield a 0.15 μm thick charge generating layer.

Subsequently, a coating liquid for forming a hole transport layer was prepared by dissolving 8 parts of the compound (hole transport material) expressed by the following formula (I) and 10 parts of a polyarylate resin having a structural unit expressed by the following formula (II) in a mixed solvent containing 40 parts of dimethoxymethane and 60 parts of chlorobenzene. The weight average molecular weight (Mw) of the polyarylate resin was 100000. The resulting coating liquid was applied to the surface of the charge generating layer by immersion. The resulting coating film was dried at 120° C. for 40 minutes to yield a 15 μm thick hole transport layer.

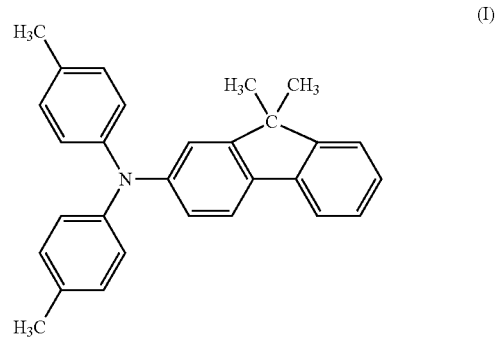

(I)

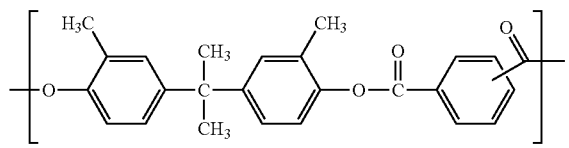

(II)

Thus, an electrophotographic photosensitive member was produced which had the electroconductive layer, the undercoat layer, the charge generating layer and the hole transporting layer on the support member.

The electrophotographic photosensitive member was installed in a printer modified from Canon laser printer (product name: LBP-2510) and subjected to surface potential measurement and evaluation of output images under the conditions of 23° C. and 50% RH. The printer was modified to a roller contact DC charge type from a primary charge type, to a process speed of 120 mm/s, and so as to perform laser exposure. More specifically, the evaluation was performed as below.

Surface Potential Measurement

A cyan process cartridge of the above-mentioned laser beam printer was modified by attaching a potential probe (Model 6000B-8 manufactured by Trek Japan) to the developing position. Then, the potential at the center of the electrophotographic photosensitive member was measured with a surface electrometer (Model 344, manufactured by Trek Japan). The surface potential of the electrophotographic photosensitive member was set so that the initial potential could be −600 V (Vd) at a dark portion and −150 V (Vl) at a light portion by controlling the amount of light to expose images.

Subsequently, the electrophotographic photosensitive member was installed in the cyan process cartridge of the laser beam printer. This process cartridge was installed in the station for the cyan process cartridge, and images were output. First, a sheet of a white solid pattern, five sheets of a pattern for examining ghost (hereinafter referred to as ghost examination pattern), a sheet of a black solid pattern, and five sheets of the ghost examination pattern were consecutively output in that order. Next, using A4 plain paper sheets, a full color pattern (character pattern having a print coverage of 1% for each color) were output on 10,000 sheets, and then, a sheet of a white solid pattern, five sheets of the ghost examination pattern, a sheet of a black solid pattern, and five sheets of the ghost examination pattern were consecutively output in that order.

Figure 2:
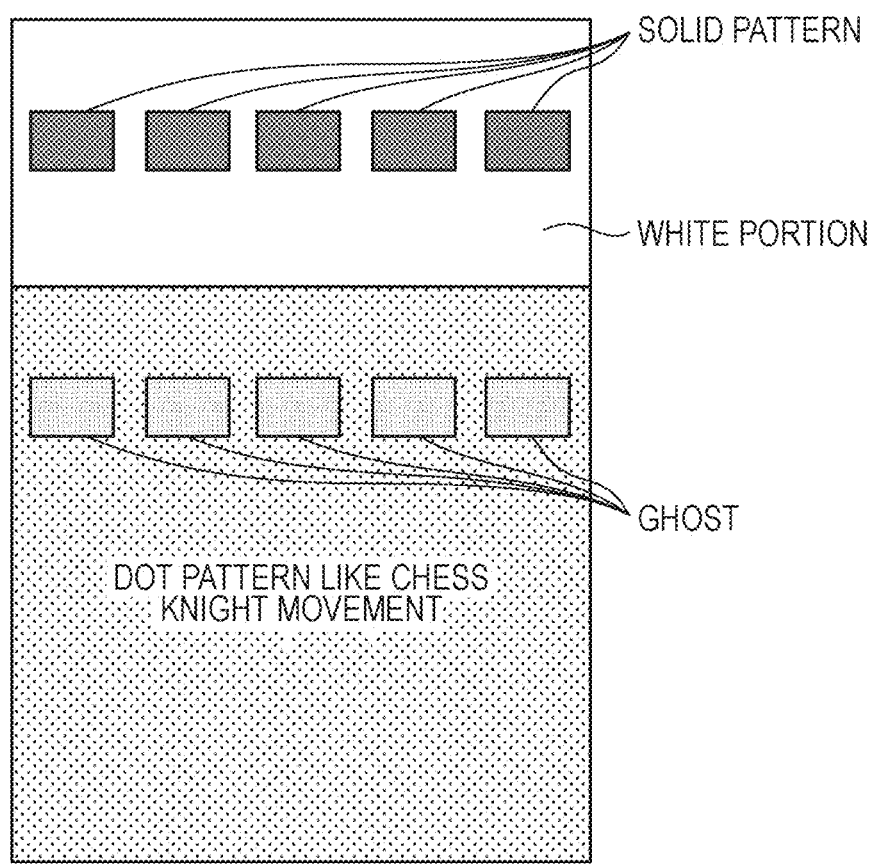
FIG. 2 is a representation illustrating a pattern for examining ghost.
Figure 3:
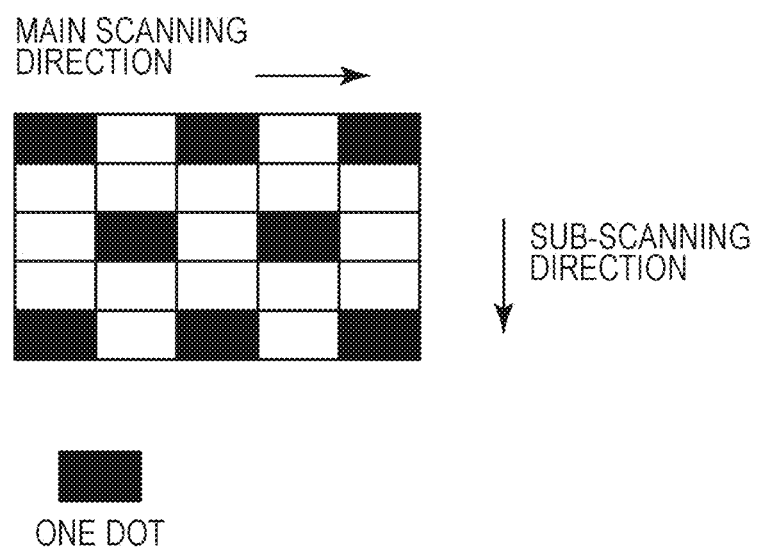
FIG. 3 is a representation of a dot pattern like chess knight (Shogi keima) movement.

The ghost examination pattern was formed as shown in FIG. 2 by printing "solid rectangles" in the white portion of the head of the sheet and then printing a halftone dot pattern like chess knight (Shogi keima) movement as shown in FIG. 3. The "ghost" portion in FIG. 2 is the portion in which ghost resulting from a solid pattern can occur.

For examining positive ghost, the difference in density between the halftone dot pattern like chess knight movement and the ghost portion was measured. More specifically, the density difference was measured at 10 points for each sheet of the ghost examination pattern, using a spectroscopic densitometer X-Rite 504/508 (manufactured by X-Rite). This operation was performed on all the 10 sheets of the ghost examination pattern. The average of density differences at 100 points in total was calculated, and the difference (initial) in Macbeth density at the initial pattern output was estimated (see the column "Initial" in Macbeth density difference in Table 12). Subsequently, the difference in Macbeth density after the output of 10,000 sheets was estimated, and the difference (variation) in Macbeth density from the initial pattern output was calculated (see the column "Variation" in Macbeth density difference in Table 12). The results are shown in Table 12. A larger difference in density (Macbeth density) suggests that a stronger positive ghost has occurred. A smaller difference in density (Macbeth density) suggests that positive ghost has been suppressed. Also, a smaller difference between the Macbeth density after the output of 10,000 sheets and the Macbeth density at the initial pattern output suggests that the ghost does not change much.

Examples 2 to 35, 38, and 39

Samples of the electrophotographic photosensitive member were produced in the same manner as in Example 1 except that the compound of general formula (1), the crosslinking agent, the resin having a polymerizable functional group, and the contents thereof were varied as shown in Table 12. Then, ghost was examined for each sample in the same manner as in Example 1. The results are shown in Table 12.

Example 36

A sample of the electrophotographic photosensitive member was produced in the same manner as in Example 1 except that the hole transport material of formula (I) was replaced with the compound expressed by the following formula (III), and ghost was examined in the same manner as in Example 1. The results are shown in Table 12.

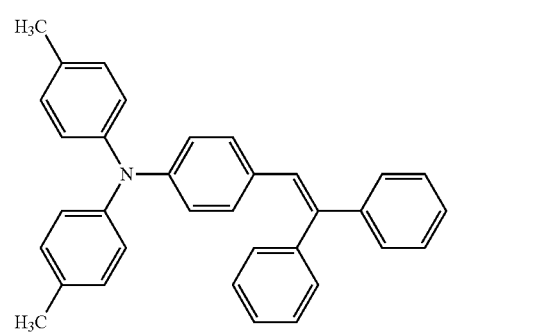

(III)

Example 37

A sample of the electrophotographic photosensitive member was produced in the same manner as in Example 1 except that the hole transport material of formula (I) was replaced with the compound expressed by the following formula (IV), and ghost was examined in the same manner as in Example 1. The results are shown in Table 12.

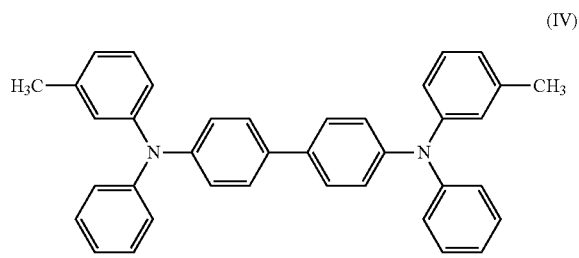

(IV)

Comparative Example 1

An electrophotographic photosensitive member was produced in the same manner as in Example 1 except that the undercoat layer was formed using the following coating liquid, and ghost was examined in the same manner as in Example 1. The results are shown in Table 12.

The coating liquid for the undercoat layer was prepared by dissolving 3 parts of the compound expressed by the following formula (V) and 7 parts of polyamide resin (Amilan CM8000, produced by Toray) in a mixed solution containing 120 parts of butanol, 100 parts of methanol and 30 parts of DMF (N,N-dimethylformamide).

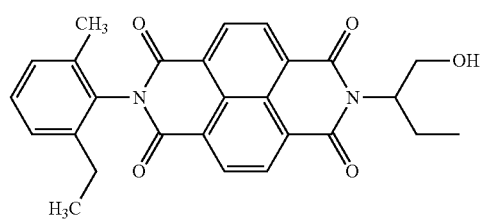

(V)

Comparative Example 2

An electrophotographic photosensitive member was produced in the same manner as in Example 1 except that the undercoat layer was formed using the following coating liquid, and ghost was examined in the same manner as in Example 1. The results are shown in Table 12.

The coating liquid for the undercoat layer was prepared by dissolving 5 parts of the compound expressed by the following formula (VI) and 5 parts of polyamide resin (Amilan CM8000, produced by Toray) in a mixed solution containing 120 parts of butanol, 100 parts of methanol and 30 parts of DMF.

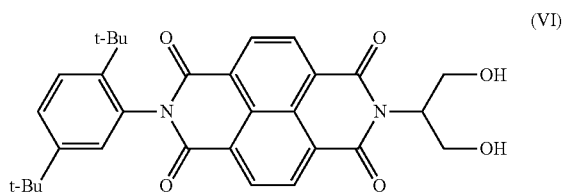 [SMILES: CC(C)(C)c1ccc(C(C)(C)C)c(N2C(=O)c3ccc4c5c(ccc(c35)C2=O)C(=O)N(C(CO)CO)C4=O)c1]

(VI)

Comparative Example 3

An electrophotographic photosensitive member was produced in the same manner as in Example 1 except that the undercoat layer was formed using the following coating liquid, and ghost was examined in the same manner as in Example 1. The results are shown in Table 12.

The coating liquid for the undercoat layer was prepared by dissolving 10 parts of the compound expressed by the following formula (VII) and 5 parts of phenol resin (PL-4804, produced by GUN EI Chemical Industry) in a mixed solution containing 200 parts of dimethylformamide and 150 parts of benzyl alcohol.

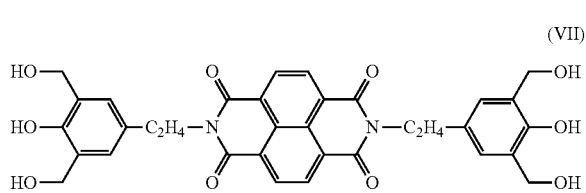

(VII)

Comparative Example 4

An electrophotographic photosensitive member was produced in the same manner as in Example 1 except that the undercoat layer was formed using the following coating liquid, and ghost was examined in the same manner as in Example 1. The results are shown in Table 12.

The coating liquid for the undercoat layer was prepared by mixing 25 parts of the compound expressed by the following formula (VIII), 25 parts of polycarbonate (PCZ-200, produced by Mitsubishi Gas Chemical Company), and 200 parts of toluene in a ball mill for 50 hours for dispersing the materials in each other.

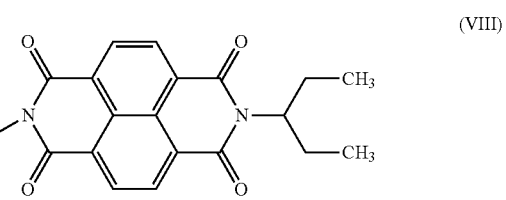

(VIII)

Comparative Example 5

An electrophotographic photosensitive member was produced in the same manner as in Example 1 except that the undercoat layer was formed using the following coating liquid, and ghost was examined in the same manner as in Example 1. The results are shown in Table 12

The coating liquid for the undercoat layer was prepared by dissolving 8 parts of the compound expressed by formula (V), 1.5 parts of a polyvinyl acetal resin (product name: BX-1, produced by Sekisui Chemical), and 0.0005 part of zinc (II) octylate as a catalyst in a mixed solvent containing 100 parts of dimethylacetamide and 100 parts of tetrahydrofuran. To the resulting solution, blocked isocyanate (product name: BL 3175, produced by Sumika Bayer Urethane) was added in an amount of 6 parts in terms of solid to prepare the coating liquid.

TABLE 12

Electrophotographic Photosensitive Member Production Conditions and Evaluation Results

| Example No. | Imide compound Item | parts | Crosslinking agent Item | parts | Resin Item | Parts | Ratio of total mass of crosslinking agent and resin to mass of imide compound | Macbeth density difference Initial | Variation |
|---|---|---|---|---|---|---|---|---|---|
| Example 1 | Exemplified compound 101 | 100 | Crosslinking agent 1 | 150 | Resin 1 | 3.8 | 1.54 | 0.025 | 0.005 |
| Example 2 | Exemplified compound 104 | 100 | Crosslinking agent 1 | 150 | Resin 1 | 3.8 | 1.54 | 0.022 | 0.003 |
| Example 3 | Exemplified compound 105 | 100 | Crosslinking agent 1 | 150 | Resin 1 | 3.8 | 1.54 | 0.027 | 0.007 |
| Example 4 | Exemplified compound 108 | 100 | Crosslinking agent 1 | 150 | Resin 1 | 3.8 | 1.54 | 0.035 | 0.015 |
| Example 5 | Exemplified compound 109 | 100 | Crosslinking agent 2 | 150 | Resin 2 | 3.8 | 1.54 | 0.020 | 0.002 |
| Example 6 | Exemplified compound 110 | 100 | Crosslinking agent 2 | 150 | Resin 2 | 3.8 | 1.54 | 0.025 | 0.006 |
| Example 7 | Exemplified compound 111 | 100 | Crosslinking agent 2 | 150 | Resin 2 | 3.8 | 1.54 | 0.038 | 0.012 |
| Example 8 | Exemplified compound 112 | 100 | Crosslinking agent 1 | 150 | Resin 1 | 3.8 | 1.54 | 0.038 | 0.016 |
| Example 9 | Exemplified compound 116 | 100 | Crosslinking agent 1 | 150 | Resin 3 | 3.8 | 1.54 | 0.025 | 0.007 |
| Example 10 | Exemplified compound 120 | 100 | Crosslinking agent 1 | 150 | Resin 3 | 3.8 | 1.54 | 0.024 | 0.007 |
| Example 11 | Exemplified compound 121 | 100 | Crosslinking agent 1 | 150 | Resin 3 | 3.8 | 1.54 | 0.038 | 0.015 |
| Example 12 | Exemplified compound 124 | 100 | Crosslinking agent 1 | 150 | Resin 3 | 3.8 | 1.54 | 0.026 | 0.006 |
| Example 13 | Exemplified compound 137 | 100 | Crosslinking agent 1 | 150 | Resin 1 | 3.8 | 1.54 | 0.044 | 0.022 |
| Example 14 | Exemplified compound 139 | 100 | Crosslinking agent 2 | 150 | Resin 2 | 3.8 | 1.54 | 0.034 | 0.011 |
| Example 15 | Exemplified compound 140 | 100 | Crosslinking agent 2 | 150 | Resin 2 | 3.8 | 1.54 | 0.034 | 0.012 |
| Example 16 | Exemplified compound 142 | 100 | Crosslinking agent 2 | 150 | Resin 2 | 3.8 | 1.54 | 0.033 | 0.014 |
| Example 17 | Exemplified compound 101 | 100 | Crosslinking agent 1 | 212 | Resin 2 | 38 | 2.50 | 0.022 | 0.008 |
| Example 18 | Exemplified compound 101 | 100 | Crosslinking agent 1 | 30 | Resin 2 | 20 | 0.50 | 0.026 | 0.008 |
| Example 19 | Exemplified compound 105 | 100 | Crosslinking agent 3 | 150 | Resin 1 | 3.8 | 1.54 | 0.026 | 0.009 |
| Example 20 | Exemplified compound 105 | 100 | Crosslinking agent 4 | 150 | Resin 1 | 3.8 | 1.54 | 0.023 | 0.005 |
| Example 21 | Exemplified compound 101 | 100 | Crosslinking agent 1 | 150 | — | 0 | 1.50 | 0.036 | 0.011 |
| Example 22 | Exemplified compound 201 | 100 | Crosslinking agent 1 | 150 | Resin 1 | 3.8 | 1.54 | 0.025 | 0.006 |
| Example 23 | Exemplified compound 203 | 100 | Crosslinking agent 1 | 150 | Resin 1 | 3.8 | 1.54 | 0.033 | 0.016 |
| Example 24 | Exemplified compound 204 | 100 | Crosslinking agent 1 | 150 | Resin 1 | 3.8 | 1.54 | 0.027 | 0.019 |
| Example 25 | Exemplified compound 206 | 100 | Crosslinking agent 1 | 150 | Resin 1 | 3.8 | 1.54 | 0.027 | 0.008 |
| Example 26 | Exemplified compound 222 | 100 | Crosslinking agent 1 | 150 | Resin 1 | 3.8 | 1.54 | 0.046 | 0.025 |
| Example 27 | Exemplified compound 201 | 100 | Crosslinking agent 1 | 150 | — | 0 | 1.50 | 0.034 | 0.013 |
| Example 28 | Exemplified compound 301 | 100 | Crosslinking agent 2 | 150 | Resin 2 | 3.8 | 1.54 | 0.024 | 0.007 |
| Example 29 | Exemplified compound 302 | 100 | Crosslinking agent 2 | 150 | Resin 2 | 3.8 | 1.54 | 0.035 | 0.015 |
| Example 30 | Exemplified compound 303 | 100 | Crosslinking agent 2 | 150 | Resin 2 | 3.8 | 1.54 | 0.023 | 0.008 |
| Example 31 | Exemplified compound 305 | 100 | Crosslinking agent 2 | 150 | Resin 2 | 3.8 | 1.54 | 0.023 | 0.007 |
| Example 32 | Exemplified compound 308 | 100 | Crosslinking agent 2 | 150 | Resin 2 | 3.8 | 1.54 | 0.027 | 0.007 |
| Example 33 | Exemplified compound 316 | 100 | Crosslinking agent 2 | 150 | Resin 2 | 3.8 | 1.54 | 0.046 | 0.023 |

TABLE 12-continued

Electrophotographic Photosensitive Member Production Conditions and Evaluation Results

| | Imide compound | | Crosslinking agent | | Resin | | Ratio of total mass of crosslinking agent and resin to mass of imide compound | Macbeth density difference | |
|---|---|---|---|---|---|---|---|---|---|
| Example No. | Item | parts | Item | parts | Item | Parts | | Initial | Variation |
| Example 34 | Exemplified compound 317 | 100 | Crosslinking agent 2 | 150 | Resin 2 | 3.8 | 1.54 | 0.050 | 0.025 |
| Example 35 | Exemplified compound 301 | 100 | Crosslinking agent 2 | 150 | — | 0 | 1.50 | 0.037 | 0.010 |
| Example 36 | Exemplified compound 101 | 100 | Crosslinking agent 1 | 150 | Resin 1 | 3.8 | 1.54 | 0.023 | 0.005 |
| Example 37 | Exemplified compound 101 | 100 | Crosslinking agent 1 | 150 | Resin 1 | 3.8 | 1.54 | 0.025 | 0.005 |
| Example 38 | Exemplified compound 101 | 100 | Crosslinking agent 1 | 242 | Resin 2 | 18 | 2.60 | 0.042 | 0.018 |
| Example 39 | Exemplified compound 101 | 100 | Crosslinking agent 1 | 45 | Resin 2 | 2 | 0.47 | 0.040 | 0.019 |
| Comparative Example 1 | Compound (8) | 100 | — | 0 | Polyamide resin | 233 | 2.33 | 0.060 | 0.067 |
| Comparative Example 2 | Compound (9) | 100 | — | 0 | Polyamide resin | 100 | 1.00 | 0.059 | 0.065 |
| Comparative Example 3 | Compound (10) | 100 | — | 0 | Phenol resin | 50 | 0.50 | 0.063 | 0.058 |
| Comparative Example 4 | Compound (11) | 100 | — | 0 | Polycarbonate resin | 100 | 1.00 | 0.058 | 0.041 |
| Comparative Example 5 | Compound (8) | 200 | Crosslinking agent 1 | 150 | Resin 1 | 3.8 | 0.77 | 0.055 | 0.050 |

In Table 12, crosslinking agent 1 is an isocyanate-based agent (solid content: 60%) named DESMODUR BL 3175 produced by Sumika Bayer Urethane). Crosslinking agent 2 is an isocyanate-based agent (solid content: 60%) named DESMODUR BL 3575 produced by Sumika Bayer Urethane). Crosslinking agent 3 is a butylated melamine-based agent having an alkyletherified N-methylol group (solid content: 60%) named Super Beckamine J 821-60 produced by DIC. Crosslinking agent 4 is a butylated urea-based agent having an alkyletherified N-methylol group (solid content: 60%) named Beckamine P 138 produced by DIC.

In Table 12, resin 1 (resin having a polymerizable functional group) is a polyvinyl acetal resin containing 3.3 mmol of hydroxy per 1 g and having a molecular weight of $1 \times 10^5$. Resin 2 is a polyvinyl acetal resin containing 3.3 mmol of hydroxy per 1 g and having a molecular weight of $2 \times 10^4$. Resin 3 is a polyvinyl acetal resin containing 2.5 mmol of hydroxy per 1 g and having a molecular weight of $3.4 \times 10^5$.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-217359, filed Oct. 24, 2014, which is hereby incorporated by reference herein in its entirety.

What is claimed is:
1. An electrophotographic photosensitive member comprising in the following order:
    a support member;
    an undercoat layer adjacent to the support member; and
    a photosensitive layer adjacent to the undercoat layer,
    wherein the undercoat layer contains a polymer produced by polymerizing a composition containing a crosslinking agent and the compound expressed by general formula (1):

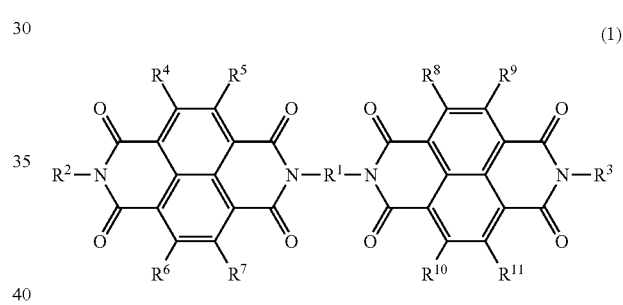

(1)

wherein $R^1$ represents one selected from the group consisting of formula (2) and formula (3):

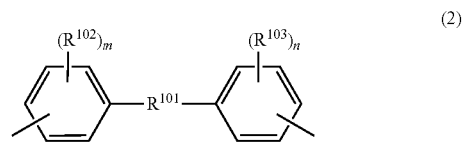

(2)

wherein $R^{101}$ represents one selected from the group consisting of O, S, SO$_2$, NR$^{104}$ where R$^{104}$ is selected from the group consisting of hydrogen atom, alkyl group and aryl group, carbonyl group, alkylene group, and arylene group, and the alkylene group and the arylene group each may have a substituent selected from the group consisting of alkyl group having a carbon number in the range of 1 to 5, phenyl group, and halogen atoms, and wherein $R^{102}$ and $R^{103}$ each represent one selected from the group consisting of alkyl group having a carbon number in the range of 1 to 3, alkoxy group, alkoxycarbonyl group, cyano group, nitro group, and halogen atoms, and m being the number of $R^{102}$ and n being the number of $R^{103}$ each represent an integer of 0 to 4 and may be the same as or different from each other;

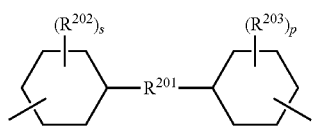

(3)

wherein $R^{201}$ represent one selected from the group consisting of O, S, $SO_2$, $NR^{204}$ where $R^{204}$ is selected from hydrogen atom, alkyl group and aryl group, carbonyl group, alkylene group, and arylene group, and the alkylene group and the arylene group each may have a substituent selected from the group consisting of alkyl group having a carbon number in the range of 1 to 5, phenyl group, and halogen atoms, and wherein $R^{202}$ and $R^{203}$ each represent one selected from the group consisting of alkyl group having a carbon number of 1 or 2, alkoxy group, alkoxycarbonyl group, and halogen atoms, and s being the number of $R^{202}$ and p being the number of $R^{203}$ each represent an integer of 1 to 4 and may be the same as or different from each other, wherein $R^2$ and $R^3$ each independently represent one selected from the group consisting of alkyl group, aryl group, and alkyl-derived groups having a main chain in which one of the carbon atoms is replaced with a species selected from the group consisting of O, S, and $NR^{13}$ where $R^{13}$ is selected from hydrogen atom and alkyl group, and $R^2$ and $R^3$ has a polymerizable functional group selected from the group consisting of hydroxy group, thiol group, amino group and carboxy group, and wherein $R^4$ to $R^{11}$ each independently represent one selected from the group consisting of hydrogen atom, halogen atoms, cyano group, nitro group, alkyl group, and aryl group, and the alkyl group and the aryl group each may have a substituent selected from the group consisting of alky group, acyl group, alkoxy group, alkoxycarbonyl group, cyano group, nitro group, and halogen atoms.

2. The electrophotographic photosensitive member according to claim 1, wherein $R^2$ and $R^3$ in general formula (1) are each expressed by formula (5):

(5)

wherein $R^{401}$ represents hydrogen atom, $R^{402}$ and $R^{403}$ each represent one of alkyl group and aryl group, and each of the alkyl group and the aryl group has hydroxy group and may have at least one substituent selected from the group consisting of alkyl group having a carbon number of 1 to 6, alkoxy group, alkoxycarbonyl group, phenyl group, and halogen atoms.

3. The electrophotographic photosensitive member according to claim 1, wherein the crosslinking agent is a compound selected from the group consisting of isocyanate compounds having an isocyanate group or a blocked isocyanate group, and amine compounds having an N-methylol group or an alkyletherified N-methylol group.

4. The electrophotographic photosensitive member according to claim 1, wherein the composition further contains a resin having a polymerizable functional group.

5. The electrophotographic photosensitive member according to claim 4, wherein the ratio of the total mass of the crosslinking agent and the resin having the polymerizable functional group in the composition is in the range of 0.5 to 2.5 relative to the mass of the compound expressed by general formula (1) in the composition.

* * * * *